United States Patent
Offen et al.

(10) Patent No.: US 9,598,478 B2
(45) Date of Patent: Mar. 21, 2017

(54) PEPTIDES FOR THE TREATMENT OF NEURODEGENERATIVE DISEASES

(71) Applicant: Ramot at Tel-Aviv University Ltd., Tel-Aviv (IL)

(72) Inventors: Daniel Offen, Kfar HaRoe (IL); Israel Aharony, Givat Shmuel (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

(21) Appl. No.: 14/433,047

(22) PCT Filed: Mar. 5, 2013

(86) PCT No.: PCT/IL2013/050196
§ 371 (c)(1),
(2) Date: Apr. 2, 2015

(87) PCT Pub. No.: WO2014/057484
PCT Pub. Date: Apr. 17, 2014

(65) Prior Publication Data
US 2015/0259392 A1 Sep. 17, 2015

Related U.S. Application Data

(60) Provisional application No. 61/711,309, filed on Oct. 9, 2012.

(51) Int. Cl.
C07K 14/47 (2006.01)
A61K 38/00 (2006.01)

(52) U.S. Cl.
CPC .......... *C07K 14/4703* (2013.01); *C07K 14/47* (2013.01); *A61K 38/00* (2013.01); *C07K 2319/10* (2013.01)

(58) Field of Classification Search
None
See application file for complete search history.

(56) References Cited

FOREIGN PATENT DOCUMENTS

| WO | WO 2010/017408 | 2/2010 |
|---|---|---|
| WO | WO 2010/021822 | 2/2010 |
| WO | WO 2014/057484 | 4/2014 |

OTHER PUBLICATIONS

Merck Manual (https://www.merckmanuals.com/home/infections/bacteremia,-sepsis,-and-septic-shock/sepsis,-severe-sepsis,-and-septic-shock , accessed Mar. 17, 2016).*
UCSF(http://memory.ucsf.edu/education/diseases , accessed Mar. 17, 2016).*
Merck Manual, ALS (https://www.merckmanuals.com/home/brain,-spinal-cord,-and-nerve-disorders/peripheral-nerve-disorders/amyotrophic-lateral-sclerosis-and-other-motor-neuron-diseases accessed Mar. 17, 2016).*
International Preliminary Report on Patentability Dated Apr. 23, 2015 From the International Bureau of WIPO Re. Application No. PCT/IL2013/050196.
International Search Report and the Written Opinion Dated Jun. 19, 2013 From the International Searching Authority Re. Application No. PCT/IL2013/050196.
Aharony et al. "ED11—A Novel Huntington Based Peptide as A CASPASE-6 Inhibitor", Journal of Neurology, Neurosurgery & Psychiatry, 83(Suppl.1): A53, #PO5, Sep. 30, 2012.
Cattaneo et al. "Normal Huntingtin Function: An Alternative Approach to Huntington's Disease", Nature Reviews Neuroscience, 6: 919-930, Dec. 2005.
Graham et al. "Cleavage at the 586 Amino Acid Caspase-6 Site in Mutant Huntingtin Influences Caspase-6 Activation In Vivo", The Journal of Neuroscience, 30(45): 15019-15029, Nov. 10, 2010. p. 15020, Left Col., 3rd Para, p. 15024, Right Col., Last Para, Fig.6, p. 15026, Left Col., Last Para, p. 15027, Left Col., Last Para.
Stennicke et al. "Internally Quenched Fluorescent Peptide Substrates Disclose the Subsite Preferences of Human Caspases 1, 3, 6, 7 and 8", Biochemistry Journal, 350: 563-568, 2000.
Warby et al. "Activated Caspase-6 and Caspase-6-Cleaved Fragments of Huntingtin Specifically Colocalize in the Nucleus", Human Molecular Genetics, 17(15): 2390-2404, 2008.
Wellington et al. "Inhibiting Caspase Cleavage of Huntingtin Reduces Toxicity and Aggregate Formation in Neuronal and Non-neuronal Cells", The Journal of Biological Chemistry, 275(26): 19831-19838, Jun. 30, 2000. p. 19833, Right Col., Para 1-3, Fig.4.
Supplementary European Search Report and the European Search Opinion Dated Apr. 19, 2016 From the European Patent Office Re. Application No. 13844958.2.
Aharony et al. "A Huntingtin Based Peptide Inhibitor of Caspase-6 Provides Protection From Mutant Huntingtin Induced Motor and Behavioral Deficits", Human Molecular Genetics, XP055263909, 24(9): 2604-2614, Advance Access Publication Jan. 23, 2015.
Rezessy-Szabo et al. "A Novel Thermostable Alpha-Galactosidase From the Thermophilic Fungus Thermomyces Lanoginosus CBS 395.62/b: Purification and Characterization", Biochimica et Biophysica Acta, XP005805917, 1770(1): 55-62, Available Online Aug. 1, 2006. Fig.7.

* cited by examiner

*Primary Examiner* — James H Alstrum Acevedo
*Assistant Examiner* — Tara Martinez

(57) ABSTRACT

An isolated peptide comprising a Huntingtin (Htt) amino acid sequence being no longer than 15 amino acids, wherein said Htt amino acid sequence comprises the sequence $X_1 X_2 X_3 X_4 X_5$, wherein $X_1$ is a hydrophobic amino acid or threonine, $X_2$ is a hydrophobic amino acid, $X_3$ is a hydrophobic amino acid, $X_4$ is an acidic amino acid and $X_5$ is selected from the group consisting of glycine, serine and alanine, the peptide capable of specifically inhibiting the activity of caspase 6.

10 Claims, 12 Drawing Sheets
(2 of 12 Drawing Sheet(s) Filed in Color)

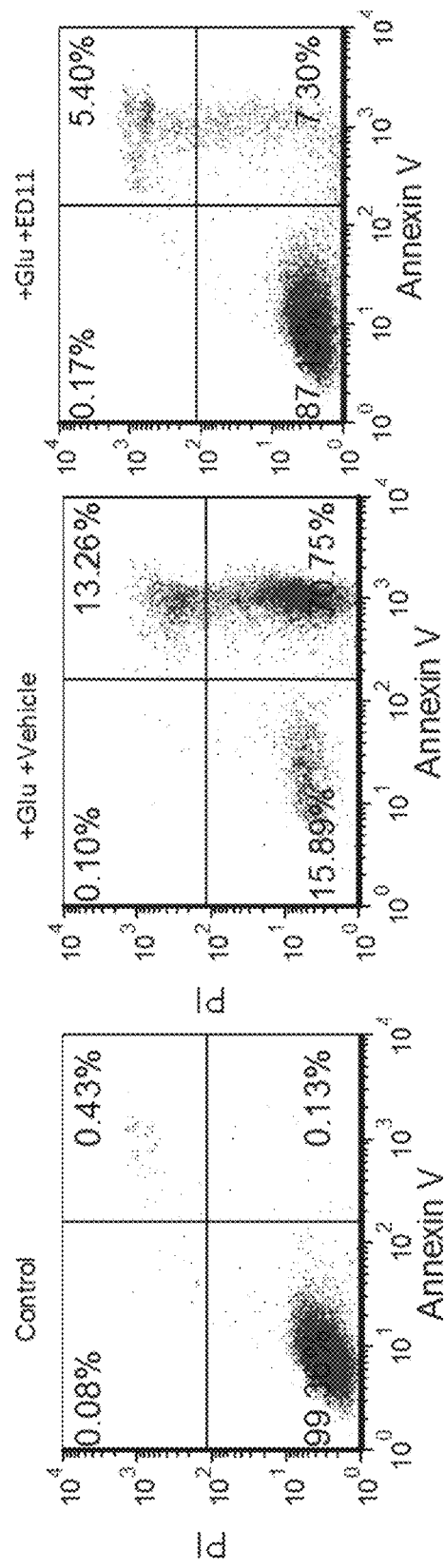

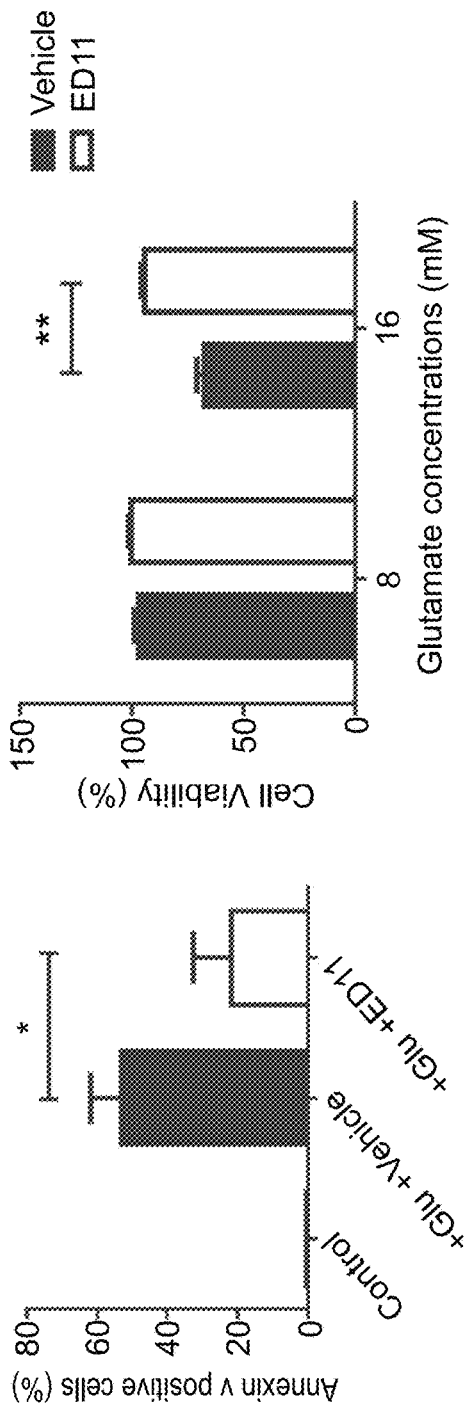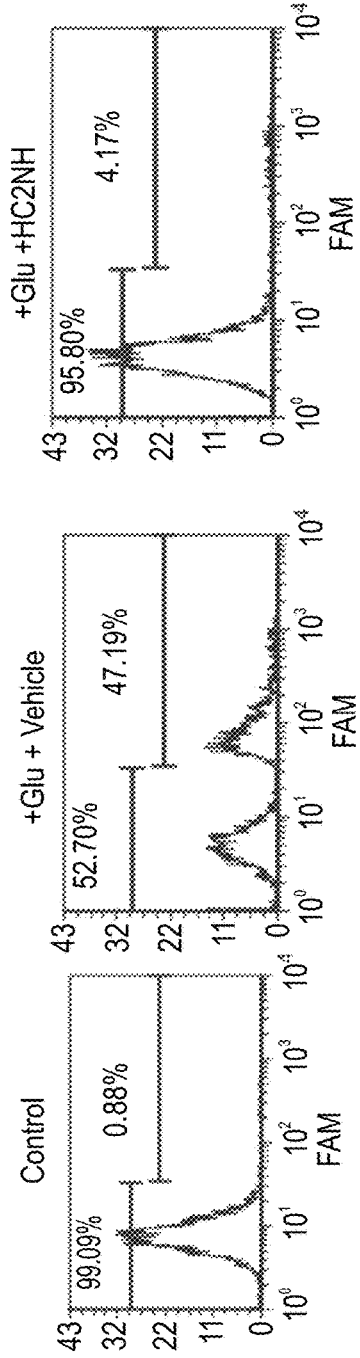
FIG. 3B
FIG. 3C
FIG. 3D

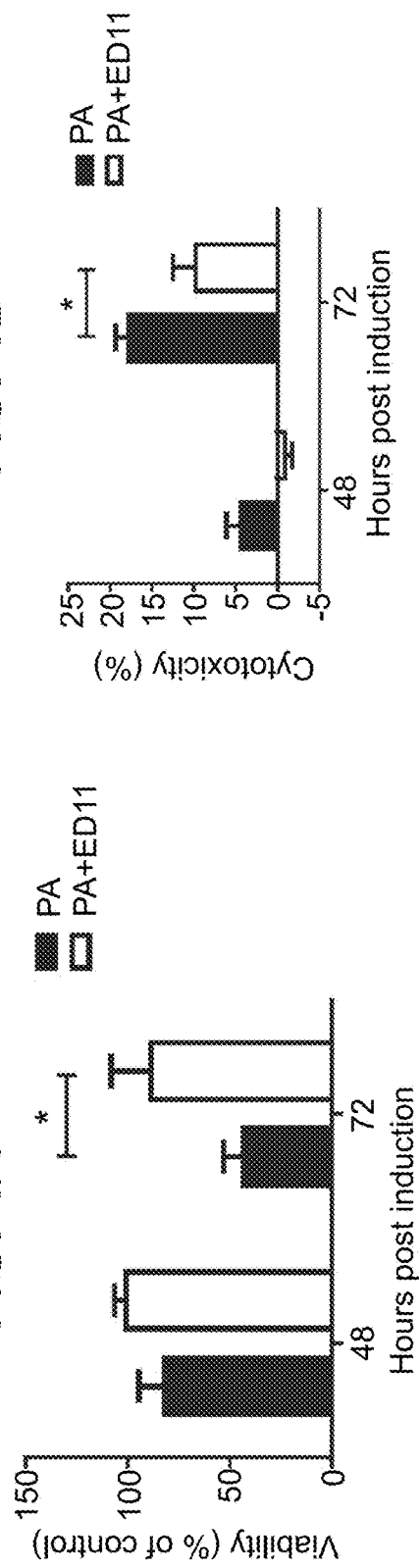
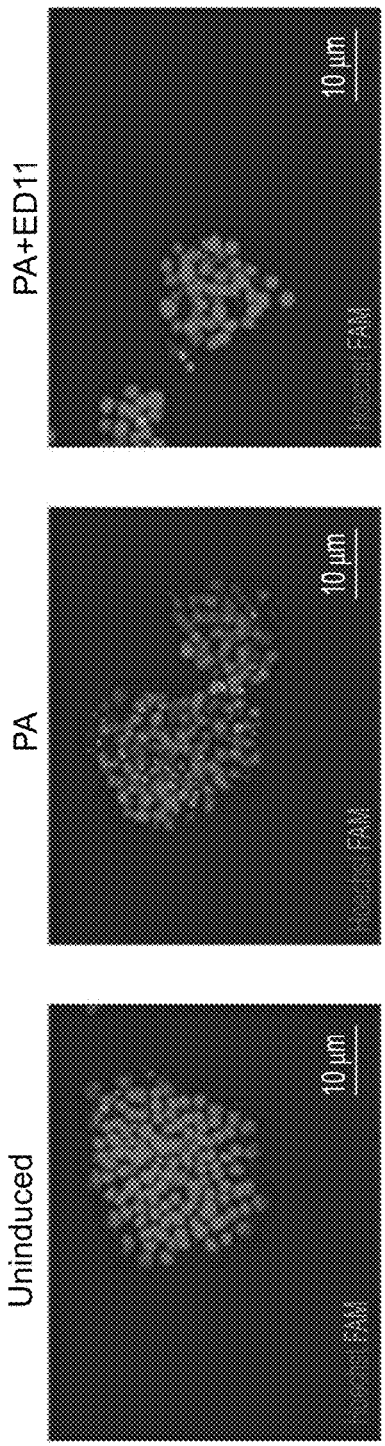
FIG. 4A
FIG. 4B
FIG. 4C

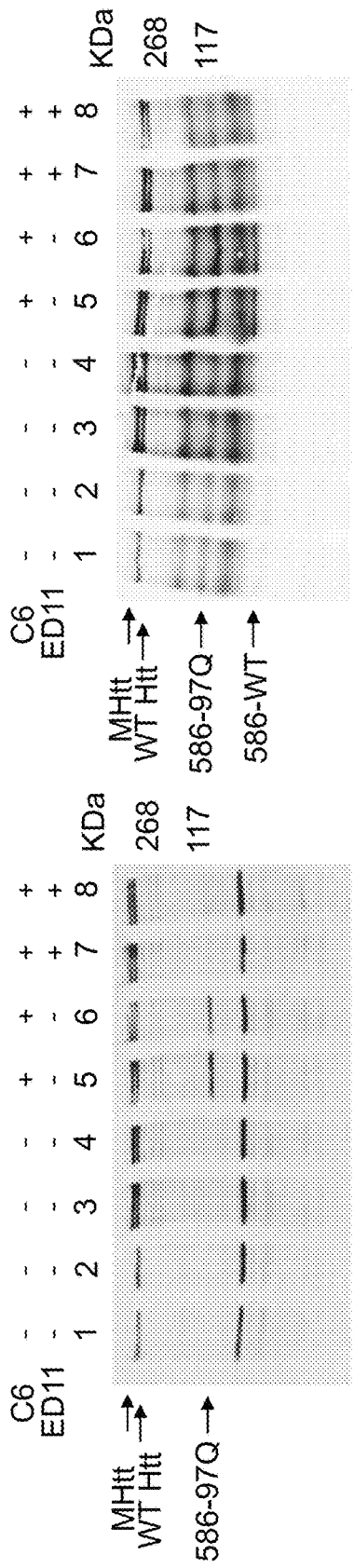

SEQUENCE LISTING

<160> NUMBER OF SEQ ID NOS: 36

<210> SEQ ID NO 1
<211> LENGTH: 4
<212> TYPE: PRT
<213> ORGANISM: Artificial sequence
<220> FEATURE:
<223> OTHER INFORMATION: Synthetic peptide

<400> SEQUENCE: 1

Ile Val Leu Asp
1

<210> SEQ ID NO 2
<211> LENGTH: 8
<212> TYPE: PRT
<213> ORGANISM: Artificial sequence
<220> FEATURE:
<223> OTHER INFORMATION: Synthetic peptide

<400> SEQUENCE: 2

Ile Val Leu Asp Gly Thr Asp Asn
1               5

<210> SEQ ID NO 3
<211> LENGTH: 7
<212> TYPE: PRT
<213> ORGANISM: Artificial sequence
<220> FEATURE:
<223> OTHER INFORMATION: Synthetic peptide

<400> SEQUENCE: 3

Ile Val Leu Asp Gly Thr Asp
1               5

<210> SEQ ID NO 4
<211> LENGTH: 6
<212> TYPE: PRT
<213> ORGANISM: Artificial sequence
<220> FEATURE:
<223> OTHER INFORMATION: Synthetic peptide

<400> SEQUENCE: 4

Ile Val Leu Asp Gly Thr
1               5

<210> SEQ ID NO 5
<211> LENGTH: 5
<212> TYPE: PRT
<213> ORGANISM: Artificial sequence
<220> FEATURE:
<223> OTHER INFORMATION: Synthetic peptide

<400> SEQUENCE: 5

Ile Val Leu Asp Gly
1               5

<210> SEQ ID NO 6
<211> LENGTH: 24
<212> TYPE: PRT
<213> ORGANISM: Artificial sequence
<220> FEATURE:
<223> OTHER INFORMATION: Example of a peptide which include both the Htt
      sequence and the cell penetrating peptide

<400> SEQUENCE: 6

Gly Arg Lys Lys Arg Arg Gln Arg Arg Pro Pro Gln Ser Ser Glu
1               5                   10                  15

Ile Val Leu Asp Gly Thr Asp Asn
            20

<210> SEQ ID NO 7
<211> LENGTH: 13
<212> TYPE: PRT
<213> ORGANISM: Artificial sequence
<220> FEATURE:
<223> OTHER INFORMATION: Example of a cell penetrating peptide

<400> SEQUENCE: 7

Gly Arg Lys Lys Arg Arg Gln Arg Arg Arg Pro Pro Gln
1               5                   10

<210> SEQ ID NO 8
<211> LENGTH: 12
<212> TYPE: PRT
<213> ORGANISM: Artificial sequence
<220> FEATURE:
<223> OTHER INFORMATION: Example of a cell penetrating peptide

<400> SEQUENCE: 8

```
Gly Arg Lys Lys Arg Arg Gln Arg Arg Pro Pro
1               5                   10
```

<210> SEQ ID NO 9
<211> LENGTH: 11
<212> TYPE: PRT
<213> ORGANISM: Artificial sequence
<220> FEATURE:
<223> OTHER INFORMATION: Example of a cell penetrating peptide

<400> SEQUENCE: 9

```
Gly Arg Lys Lys Arg Arg Gln Arg Arg Pro
1               5                   10
```

<210> SEQ ID NO 10
<211> LENGTH: 10
<212> TYPE: PRT
<213> ORGANISM: Artificial sequence
<220> FEATURE:
<223> OTHER INFORMATION: Example of a cell penetrating peptide

<400> SEQUENCE: 10

```
Gly Arg Lys Lys Arg Arg Gln Arg Arg
1               5                   10
```

<210> SEQ ID NO 11
<211> LENGTH: 9
<212> TYPE: PRT
<213> ORGANISM: Artificial sequence
<220> FEATURE:
<223> OTHER INFORMATION: Example of a cell penetrating peptide

<400> SEQUENCE: 11

```
Gly Arg Lys Lys Arg Arg Gln Arg Arg
1               5
```

<210> SEQ ID NO 12
<211> LENGTH: 8
<212> TYPE: PRT
<213> ORGANISM: Artificial sequence
<220> FEATURE:
<223> OTHER INFORMATION: Example of a cell penetrating peptide

<400> SEQUENCE: 12

```
Gly Arg Lys Lys Arg Arg Gln Arg
1               5
```

<210> SEQ ID NO 13
<211> LENGTH: 7
<212> TYPE: PRT
<213> ORGANISM: Artificial sequence
<220> FEATURE:
<223> OTHER INFORMATION: Example of a cell penetrating peptide

<400> SEQUENCE: 13

```
Gly Arg Lys Lys Arg Arg Gln
1               5
```

<210> SEQ ID NO 14
<211> LENGTH: 7
<212> TYPE: PRT
<213> ORGANISM: Artificial sequence
<220> FEATURE:
<223> OTHER INFORMATION: Example of a cell penetrating peptide

<400> SEQUENCE: 14

```
Tyr Gly Arg Lys Lys Arg Arg
1               5

<210> SEQ ID NO 15
<211> LENGTH: 11
<212> TYPE: PRT
<213> ORGANISM: Artificial sequence
<220> FEATURE:
<223> OTHER INFORMATION: Example of a cell penetrating peptide

<400> SEQUENCE: 15

Tyr Gly Arg Lys Lys Arg Arg Gln Arg Arg
1               5                   10

<210> SEQ ID NO 16
<211> LENGTH: 5
<212> TYPE: PRT
<213> ORGANISM: Artificial sequence
<220> FEATURE:
<223> OTHER INFORMATION: Example of a cell penetrating peptide

<400> SEQUENCE: 16

Arg Arg Gln Arg Arg
1               5

<210> SEQ ID NO 17
<211> LENGTH: 23
<212> TYPE: PRT
<213> ORGANISM: Artificial sequence
<220> FEATURE:
<223> OTHER INFORMATION: Example of a peptide which include both the Htt
      sequence and the cell penetrating peptide

<400> SEQUENCE: 17

Gly Arg Lys Lys Arg Arg Gln Arg Arg Pro Pro Gln Ser Ser Glu
1               5                   10                  15

Ile Val Leu Asp Gly Thr Asp
            20

<210> SEQ ID NO 18
<211> LENGTH: 22
<212> TYPE: PRT
<213> ORGANISM: Artificial sequence
<220> FEATURE:
<223> OTHER INFORMATION: Example of a peptide which include both the Htt
      sequence and the cell penetrating peptide

<400> SEQUENCE: 18

Gly Arg Lys Lys Arg Arg Gln Arg Arg Pro Pro Gln Ser Ser Glu
1               5                   10                  15

Ile Val Leu Asp Gly Thr
            20

<210> SEQ ID NO 19
<211> LENGTH: 21
<212> TYPE: PRT
<213> ORGANISM: Artificial sequence
<220> FEATURE:
<223> OTHER INFORMATION: Example of a peptide which include both the Htt
      sequence and the cell penetrating peptide

<400> SEQUENCE: 19

Gly Arg Lys Lys Arg Arg Gln Arg Arg Pro Pro Gln Ser Ser Glu
1               5                   10                  15

Ile Val Leu Asp Gly
            20
```

```
<210> SEQ ID NO 20
<211> LENGTH: 20
<212> TYPE: PRT
<213> ORGANISM: Artificial sequence
<220> FEATURE:
<223> OTHER INFORMATION: Example of a peptide which include both the Htt
      sequence and the cell penetrating peptide

<400> SEQUENCE: 20

Gly Arg Lys Lys Arg Arg Gln Arg Arg Arg Pro Pro Gln Ser Ser Glu
1               5                   10                  15

Ile Val Leu Asp
            20

<210> SEQ ID NO 21
<211> LENGTH: 21
<212> TYPE: PRT
<213> ORGANISM: Artificial sequence
<220> FEATURE:
<223> OTHER INFORMATION: Example of a peptide which include both the Htt
      sequence and the cell penetrating peptide

<400> SEQUENCE: 21

Gly Arg Lys Lys Arg Arg Gln Arg Arg Arg Pro Pro Gln Ile Val Leu
1               5                   10                  15

Asp Gly Thr Asp Asn
            20

<210> SEQ ID NO 22
<211> LENGTH: 23
<212> TYPE: PRT
<213> ORGANISM: Artificial sequence
<220> FEATURE:
<223> OTHER INFORMATION: Example of a peptide which include both the Htt
      sequence and the cell penetrating peptide

<400> SEQUENCE: 22

Gly Arg Lys Lys Arg Arg Gln Arg Arg Arg Pro Pro Ser Ser Glu Ile
1               5                   10                  15

Val Leu Asp Gly Thr Asp Asn
            20

<210> SEQ ID NO 23
<211> LENGTH: 22
<212> TYPE: PRT
<213> ORGANISM: Artificial sequence
<220> FEATURE:
<223> OTHER INFORMATION: Example of a peptide which include both the Htt
      sequence and the cell penetrating peptide

<400> SEQUENCE: 23

Gly Arg Lys Lys Arg Arg Gln Arg Arg Arg Pro Ser Ser Glu Ile Val
1               5                   10                  15

Leu Asp Gly Thr Asp Asn
            20

<210> SEQ ID NO 24
<211> LENGTH: 21
<212> TYPE: PRT
<213> ORGANISM: Artificial sequence
<220> FEATURE:
<223> OTHER INFORMATION: Example of a peptide which include both the Htt
      sequence and the cell penetrating peptide

<400> SEQUENCE: 24
```

```
Gly Arg Lys Lys Arg Arg Gln Arg Arg Ser Ser Glu Ile Val Leu
1               5                   10                  15

Asp Gly Thr Asp Asn
            20
```

<210> SEQ ID NO 25
<211> LENGTH: 20
<212> TYPE: PRT
<213> ORGANISM: Artificial sequence
<220> FEATURE:
<223> OTHER INFORMATION: Example of a peptide which include both the Htt
      sequence and the cell penetrating peptide

<400> SEQUENCE: 25

```
Gly Arg Lys Lys Arg Arg Gln Arg Arg Ser Ser Glu Ile Val Leu Asp
1               5                   10                  15

Gly Thr Asp Asn
            20
```

<210> SEQ ID NO 26
<211> LENGTH: 19
<212> TYPE: PRT
<213> ORGANISM: Artificial sequence
<220> FEATURE:
<223> OTHER INFORMATION: Example of a peptide which include both the Htt
      sequence and the cell penetrating peptide

<400> SEQUENCE: 26

```
Gly Arg Lys Lys Arg Arg Gln Arg Ser Ser Glu Ile Val Leu Asp Gly
1               5                   10                  15

Thr Asp Asn
```

<210> SEQ ID NO 27
<211> LENGTH: 18
<212> TYPE: PRT
<213> ORGANISM: Artificial sequence
<220> FEATURE:
<223> OTHER INFORMATION: Example of a peptide which include both the Htt
      sequence and the cell penetrating peptide

<400> SEQUENCE: 27

```
Gly Arg Lys Lys Arg Arg Gln Ser Ser Glu Ile Val Leu Asp Gly Thr
1               5                   10                  15

Asp Asn
```

<210> SEQ ID NO 28
<211> LENGTH: 18
<212> TYPE: PRT
<213> ORGANISM: Artificial sequence
<220> FEATURE:
<223> OTHER INFORMATION: Synthetic peptide

<400> SEQUENCE: 28

```
Tyr Gly Arg Lys Lys Arg Arg Ser Ser Glu Ile Val Leu Asp Gly Thr
1               5                   10                  15

Asp Asn
```

<210> SEQ ID NO 29
<211> LENGTH: 18
<212> TYPE: PRT
<213> ORGANISM: Artificial sequence
<220> FEATURE:
<223> OTHER INFORMATION: Synthetic peptide

```
<400> SEQUENCE: 29

Tyr Gly Arg Lys Lys Arg Arg Ser Ser Glu Ala Val Leu Asp Gly Thr
1               5                   10                  15

Asp Asn

<210> SEQ ID NO 30
<211> LENGTH: 18
<212> TYPE: PRT
<213> ORGANISM: Artificial sequence
<220> FEATURE:
<223> OTHER INFORMATION: Synthetic peptide

<400> SEQUENCE: 30

Tyr Gly Arg Lys Lys Arg Arg Ser Ser Glu Ile Val Leu Ala Gly Thr
1               5                   10                  15

Asp Asn

<210> SEQ ID NO 31
<211> LENGTH: 18
<212> TYPE: PRT
<213> ORGANISM: Artificial sequence
<220> FEATURE:
<223> OTHER INFORMATION: Synthetic peptide

<400> SEQUENCE: 31

Tyr Gly Arg Lys Lys Arg Arg Ser Ser Glu Ile Val Leu Asp Gly Thr
1               5                   10                  15

Ala Asn

<210> SEQ ID NO 32
<211> LENGTH: 120
<212> TYPE: PRT
<213> ORGANISM: Artificial Sequence
<220> FEATURE:
<223> OTHER INFORMATION: Amino acid sequence of huntingtin structure and
      cleavage sites

<400> SEQUENCE: 32

Ala Ala Ser Ser Gly Val Ser Thr Pro Gly Ser Ala Gly His Asp Ile
1               5                   10                  15

Ile Thr Glu Gln Pro Arg Ser Gln His Thr Leu Gln Ala Asp Ser Val
            20                  25                  30

Asp Leu Ala Ser Cys Asp Leu Thr Ser Ser Ala Thr Asp Gly Asp Glu
        35                  40                  45

Glu Asp Ile Leu Ser His Ser Ser Gln Val Ser Ala Val Pro Ser
    50                  55                  60

Asp Pro Ala Met Asp Leu Asn Asp Gly Thr Gln Ala Ser Ser Pro Ile
65                  70                  75                  80

Ser Asp Ser Ser Gln Thr Thr Thr Glu Gly Pro Asp Ser Ala Val Thr
                85                  90                  95

Pro Ser Asp Ser Ser Glu Ile Val Leu Asp Gly Thr Asp Asn Gln Tyr
            100                 105                 110

Leu Gly Leu Gln Ile Gly Gln Pro
        115                 120

<210> SEQ ID NO 33
<211> LENGTH: 5
<212> TYPE: PRT
<213> ORGANISM: Artificial Sequence
<220> FEATURE:
<223> OTHER INFORMATION: isolated peptide comprising a Huntingtin (Htt)
``` amino acid sequence capable of specifically inhibiting the
      activity of caspase 6
<220> FEATURE:
<221> NAME/KEY: MISC_FEATURE
<222> LOCATION: (1)..(1)
<223> OTHER INFORMATION: hydrophobic amino acid or threonine
<220> FEATURE:
<221> NAME/KEY: MISC_FEATURE
<222> LOCATION: (2)..(3)
<223> OTHER INFORMATION: hydrophobic amino acid
<220> FEATURE:
<221> NAME/KEY: MISC_FEATURE
<222> LOCATION: (4)..(4)
<223> OTHER INFORMATION: an acidic amino acid
<220> FEATURE:
<221> NAME/KEY: MISC_FEATURE
<222> LOCATION: (5)..(5)
<223> OTHER INFORMATION: can be either glycine, serine or alanine

<400> SEQUENCE: 33

Xaa Xaa Xaa Xaa Xaa
1               5

<210> SEQ ID NO 34
<211> LENGTH: 6
<212> TYPE: PRT
<213> ORGANISM: Artificial Sequence
<220> FEATURE:
<223> OTHER INFORMATION: Htt amino acid sequence
<220> FEATURE:
<221> NAME/KEY: MISC_FEATURE
<222> LOCATION: (1)..(1)
<223> OTHER INFORMATION: hydrophobic amino acid or threonine
<220> FEATURE:
<221> NAME/KEY: MISC_FEATURE
<222> LOCATION: (2)..(3)
<223> OTHER INFORMATION: hydrophobic amino acid
<220> FEATURE:
<221> NAME/KEY: MISC_FEATURE
<222> LOCATION: (4)..(4)
<223> OTHER INFORMATION: an acidic amino acid
<220> FEATURE:
<221> NAME/KEY: MISC_FEATURE
<222> LOCATION: (5)..(5)
<223> OTHER INFORMATION: can be either glycine, serine or alanine
<220> FEATURE:
<221> NAME/KEY: MISC_FEATURE
<222> LOCATION: (6)..(6)
<223> OTHER INFORMATION: can be either threonine, serine, asparagines or
      glutamine

<400> SEQUENCE: 34

Xaa Xaa Xaa Xaa Xaa Xaa
1               5

<210> SEQ ID NO 35
<211> LENGTH: 7
<212> TYPE: PRT
<213> ORGANISM: Artificial Sequence
<220> FEATURE:
<223> OTHER INFORMATION: Htt amino acid sequence
<220> FEATURE:
<221> NAME/KEY: MISC_FEATURE
<222> LOCATION: (1)..(1)
<223> OTHER INFORMATION: hydrophobic amino acid or threonine
<220> FEATURE:
<221> NAME/KEY: MISC_FEATURE
<222> LOCATION: (2)..(3)
<223> OTHER INFORMATION: hydrophobic amino acid
<220> FEATURE:
<221> NAME/KEY: MISC_FEATURE
<222> LOCATION: (4)..(4)
<223> OTHER INFORMATION: an acidic amino acid
<220> FEATURE:
<221> NAME/KEY: MISC_FEATURE

```
<222> LOCATION: (5)..(5)
<223> OTHER INFORMATION: can be either glycine, serine or alanine
<220> FEATURE:
<221> NAME/KEY: MISC_FEATURE
<222> LOCATION: (6)..(6)
<223> OTHER INFORMATION: can be either threonine, serine, asparagines or
      glutamine
<220> FEATURE:
<221> NAME/KEY: MISC_FEATURE
<222> LOCATION: (7)..(7)
<223> OTHER INFORMATION: can be either aspartic acid or glutamic acid

<400> SEQUENCE: 35

Xaa Xaa Xaa Xaa Xaa Xaa Xaa
1               5

<210> SEQ ID NO 36
<211> LENGTH: 8
<212> TYPE: PRT
<213> ORGANISM: Artificial Sequence
<220> FEATURE:
<223> OTHER INFORMATION: Htt amino acid sequence
<220> FEATURE:
<221> NAME/KEY: MISC_FEATURE
<222> LOCATION: (1)..(1)
<223> OTHER INFORMATION: hydrophobic amino acid or threonine
<220> FEATURE:
<221> NAME/KEY: MISC_FEATURE
<222> LOCATION: (2)..(3)
<223> OTHER INFORMATION: hydrophobic amino acid
<220> FEATURE:
<221> NAME/KEY: MISC_FEATURE
<222> LOCATION: (4)..(4)
<223> OTHER INFORMATION: an acidic amino acid
<220> FEATURE:
<221> NAME/KEY: MISC_FEATURE
<222> LOCATION: (5)..(5)
<223> OTHER INFORMATION: can be either glycine, serine or alanine
<220> FEATURE:
<221> NAME/KEY: MISC_FEATURE
<222> LOCATION: (6)..(6)
<223> OTHER INFORMATION: can be either threonine, serine, asparagines or
      glutamine
<220> FEATURE:
<221> NAME/KEY: MISC_FEATURE
<222> LOCATION: (7)..(7)
<223> OTHER INFORMATION: can be either aspartic acid or glutamic acid
<220> FEATURE:
<221> NAME/KEY: MISC_FEATURE
<222> LOCATION: (8)..(8)
<223> OTHER INFORMATION: can be either serine, asparagines, threonine or
      glutamine

<400> SEQUENCE: 36

Xaa Xaa Xaa Xaa Xaa Xaa Xaa Xaa
1               5
```

PEPTIDES FOR THE TREATMENT OF NEURODEGENERATIVE DISEASES

RELATED APPLICATIONS

This application is a National Phase of PCT Patent Application No. PCT/IL2013/050196 having International filing date of Mar. 5, 2013, which claims the benefit of priority under 35 USC §119(e) of U.S. Provisional Patent Application No. 61/711,309 filed on Oct. 9, 2012. The contents of the above applications are all incorporated by reference as if fully set forth herein in their entirety.

SEQUENCE LISTING STATEMENT

The ASCII file, entitled 62132SequenceListing.txt, created on Mar. 19, 2015, comprising 8,894 bytes, submitted concurrently with the filing of this application is incorporated herein by reference.

FIELD AND BACKGROUND OF THE INVENTION

The present invention relates to peptides for the treatment of neurodegenerative disorders and more specifically for the treatment of Huntington's disease (HD).

Huntington's disease (HD) is an autosomal dominant inherited neurodegenerative disease. The average age of onset is at 30-50 years of age. It is characterized by the progressive deterioration of cognitive and motor functions, with a fatal outcome after approximately 10-15 years of onset. HD prevalence varies between 0.5 per 100,000 in Japan, to 5-15 per 100,000 in USA and Europe. The disease was first described in 1872 by Dr. George Huntington, who published the first description of three characteristics of the disease: The heredity, the "tendency to insanity", as he observed, and age related onset.

The mutant protein involved in HD, was discovered in 1993 and was named Huntingtin (Htt). Htt is a large (340-350 kD, 3144 aa) protein that was shown to be involved in a number of cellular functions such as transcription, gastrulation, neurogenesis, neurotransmission, axonal transport, neural positioning, and apoptosis. In healthy individuals, Htt contains between 6 to 34 polyQ repeats in the N-terminus (FIG. 6). In the mutant form of Htt (mHtt), there is an extension of the polyQ repeats; a patient carrying over 40 glutamine repeats will certainly develop HD. The polyQ expansion results in the selective loss of GABAergic medium spiny striatal (MSN) neurons as well as glutamatergic cortical neurons that project into the striatum. The loss of the GABAergic MSN results in a lack of inhibitory signals from the striatum to the globus pallidus and the substantia nigra, and therefore induces excitatory signals to the neocortex. This disequilibrium is considered to be the cause for the involuntary movement symptom of the disease.

MHtt expression leads to the formation of PolyQ aggregates and inclusions, transcriptional dysregulation, excessive stimulation of glutamate receptors leading to excitotoxic neuronal damage, and the induction of apoptosis. The reduction of normal Htt activity may also contribute to disease manifestation, since normal Htt plays an important role in neuronal protection and survival and neurogenesis.

Htt was the first neuronal protein discovered to be the subject of a proteolytic cleavage by caspases. Caspase cleavage of Htt occurs at defined sites for caspase-3 at amino acids 513 and 552, caspase-2 at amino acid 552, and caspase-6 at amino acid 586 (FIG. 6). Additionally, there are two caspase-3 consensus sites at amino acids 530 and 589 that appear to be silent. Some other proteases, such as calpains, participate in Htt cleavage (FIG. 6).

Although the cleavage occur both in normal and mutant Htt, the mutant form is more susceptible to proteolysis and generates N-terminus fragments that aggregate in the cytoplasm and nucleus of neuronal cells, preceding neurodegeneration. These toxic to fragments cause additional activation of caspase-6, thus creating a positive feedback cycle of caspase activation, and induction of apoptosis.

The significance of mHtt proteolysis in HD pathogenesis is manifested by the fact that inhibiting caspase cleavage of Htt reduces toxicity and aggregates formation.

In order to reduce mHtt proteolysis, synthetic caspase inhibitors were tested on different experimental models, and indeed showed the reduction of mHtt toxicity induced in neuronal cultures and in HD animal models [Kim, M. et al., The Journal of Neuroscience, 1999, 19, 964-973: Ona, V. O et al. Nature, 1999, 399, 263-267]. These synthetic inhibitors are pseudo substrates for active caspases. They are based on small, usually 3-4 aa long peptides, conjugated to carboxy-terminal groups such as chloromethyl ketone (cmk), fluoromethyl ketone (fmk), or aldehyde (cho). These groups enable them to act as competitive inhibitors, increase the affinity to caspases and improve cell permeability and stability. These cell permeable inhibitors alkylate the active site cysteine of caspases and irreversibly block apoptosis by preventing caspase activation, substrate cleavage, and DNA ladder formation. However, most synthetic caspase inhibitors are hydrophobic and not very permeable, and could cause nonspecific toxic effects when added at concentrations required to inhibit intracellular caspases [Ona, V. O et al. Nature, 1999, 399, 263-267: Frydrych, I.; Toxicology in Vitro, Proceedings of the Scandinavian Society of Cell Toxicology 2007 Workshop, 2008, 22, 1356-1360; Zhu, S.; et al., Cell Death and Dis, Macmillan Publishers Limited, 2011, 2, e115; Chauvier, D. Cell Death Differ, 2006, 14, 387-391]. Experiments in knockout mice indicated that caspase-6 deficiency is not fatal or causes severe toxic effects.

Garcio et al (The Journal of Biological Chemistry, 273, (4): 371-376) teaches inhibition of human caspases by peptide based and macromolecular inhibitors. Nyormoi O et al., (Apoptosis. 2003 August; 8(4):371-6) teaches a synthetic peptide inhibitor of caspase 6.

SUMMARY OF THE INVENTION

According to an aspect of some embodiments of the present invention there is provided an isolated peptide comprising a Huntingtin (Htt) amino acid sequence being no longer than 15 amino acids, wherein the Htt amino acid sequence comprises the sequence $X_1X_2X_3X_4,X_5$ (SEQ ID NO: 33) wherein $X_1$ is a hydrophobic amino acid or threonine, $X_2$ is a hydrophobic amino acid, $X_3$ is a hydrophobic amino acid, $X_4$ is an acidic amino acid and $X_5$ is selected from the group consisting of glycine, serine and alanine, the peptide capable of specifically inhibiting the activity of caspase 6.

According to an aspect of some embodiments of the present invention there is provided a method of treating a caspase 6 mediated disease in a subject in need thereof, the method comprising administering to the subject a therapeutically effective amount of the isolated peptide described herein, thereby treating the caspase 6 mediated disease.

According to an aspect of some embodiments of the present invention there is provided a pharmaceutical composition comprising the isolated peptide described herein and a pharmaceutically acceptable carrier.

According to some embodiments of the invention, the $X_1$ is selected from the group consisting of isoleucine, valine, threonine, leucine, alanine, methionine, phenylalanine, tyrosine and tryptophan.

According to some embodiments of the invention, the $X_4$ is aspartic acid or glutamic acid.

According to some embodiments of the invention, the $X_2$ or $X_3$ is selected from the group consisting of isoleucine, valine, leucine, alanine, methionine, phenylalanine, tyrosine and tryptophan.

According to some embodiments of the invention, the $X_1$ is isoleucine.

According to some embodiments of the invention, the $X_2$ is valine.

According to some embodiments of the invention, the $X_3$ is leucine.

According to some embodiments of the invention, the $X_4$ is aspartic acid.

According to some embodiments of the invention, the Htt amino acid sequence comprises the sequence as set forth in SEQ ID NO: 5.

According to some embodiments of the invention, the Htt amino acid sequence comprises the sequence $X_1X_2X_3X_4X_5X_6$ (SEQ ID NO: 34), wherein $X_6$ is selected from the group consisting of threonine, serine, asparagines and glutamine.

According to some embodiments of the invention, the Htt amino acid sequence comprises the sequence $X_1X_2X_3X_4X_5X_6X_7$, (SEQ ID NO: 35) wherein $X_7$ is aspartic acid or glutamic acid.

According to some embodiments of the invention, the Htt amino acid sequence comprises the sequence $X_1X_2X_3X_4X_5X_6X_7X_8$, (SEQ ID NO: 36) wherein $X_8$ is selected from the group consisting of serine, asparagines, threonine and glutamine.

According to some embodiments of the invention, the Htt amino acid sequence comprises the amino acid sequence as set forth in SEQ ID NOs: 2-5.

According to some embodiments of the invention, the Htt amino acid sequence is attached to a cell penetrating agent.

According to some embodiments of the invention, the cell penetrating agent is a cell penetrating peptide agent.

According to some embodiments of the invention, the cell penetrating peptide agent comprises an amino acid sequence selected from the group consisting of SEQ ID NOs: 7-15 and 16.

According to some embodiments of the invention, the cell penetrating peptide agent is attached directly to the Htt amino acid sequence.

According to some embodiments of the invention, the cell penetrating peptide agent is attached to the Htt amino acid sequence via a linking amino acid sequence.

According to some embodiments of the invention, the linking amino acid sequence comprises a disulfide bridge.

According to some embodiments of the invention, the linking amino acid sequence is attached to the N terminal of the Htt amino acid sequence.

According to some embodiments of the invention, the linking amino acid sequence is attached to the C terminal of the cell penetrating peptide agent.

According to some embodiments of the invention, the linking amino acid sequence comprises the sequence SSE.

According to some embodiments of the invention, the isolated peptide comprises the sequence as set forth in SEQ ID NOs: 6 or 28.

According to some embodiments of the invention, the isolated peptide is no longer than 25 amino acids.

According to some embodiments of the invention, the peptide inhibits the activity of caspase 6 to a greater extent than it inhibits the activity of caspase 3.

According to some embodiments of the invention, the caspase 6 mediated disease is a neurodegenerative disease.

According to some embodiments of the invention, the neurodegenerative to disease is selected from the group consisting of Huntington's Disease (HD), Alzheimer's Disease (AD), aging, and stroke.

According to some embodiments of the invention, the neurodegenerative disease is HD.

According to some embodiments of the invention, the isolated peptide is for treating a caspase 6 mediated disease.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-F—ED11 inhibits caspase-6 but not caspase-3 activity in a purified caspase activity assay: A-B. Reaction development over time is inhibited in the presence of ED11 compared to vehicle or TAT-only control (A) in a dose-dependent matter (B). C. Michaelis-Menten curve shows classic competitive inhibition as Vmax stays approximately the same and Km shows a 3.3 fold increase. D. ED11 does not inhibit caspase-3 in a fluorescent caspsae-3 inhibition assay. E-F ED11 inhibits caspase-6 but not caspase-3, unlike the synthetic caspase inhibitor Z-VAD-FMK which inhibits both caspase-6 and caspase-3. Error bars represent S.E.M.

Figure 2B:
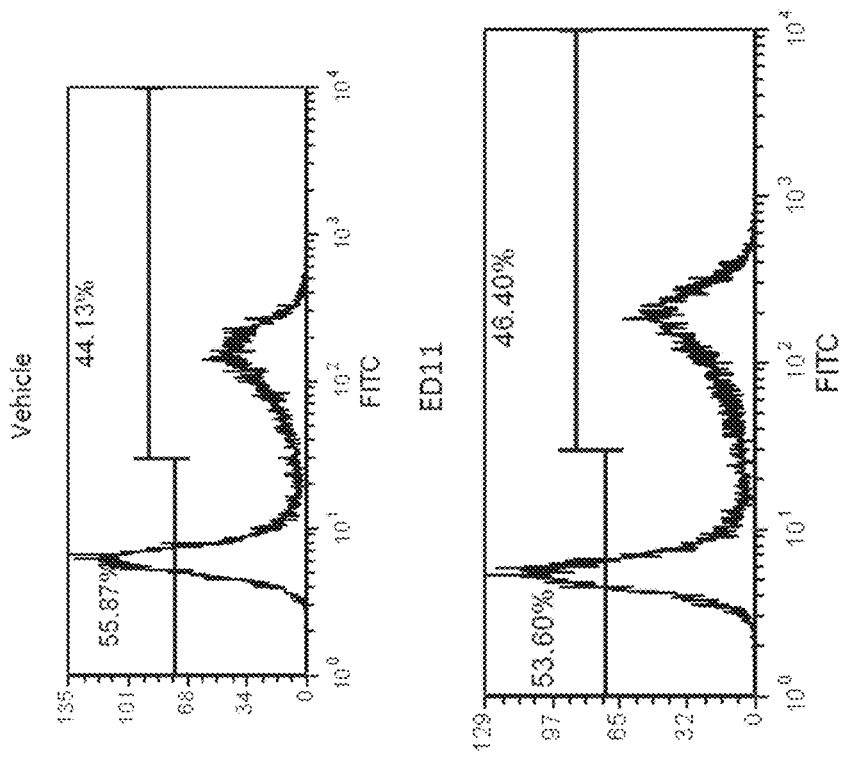
Figure 2A:
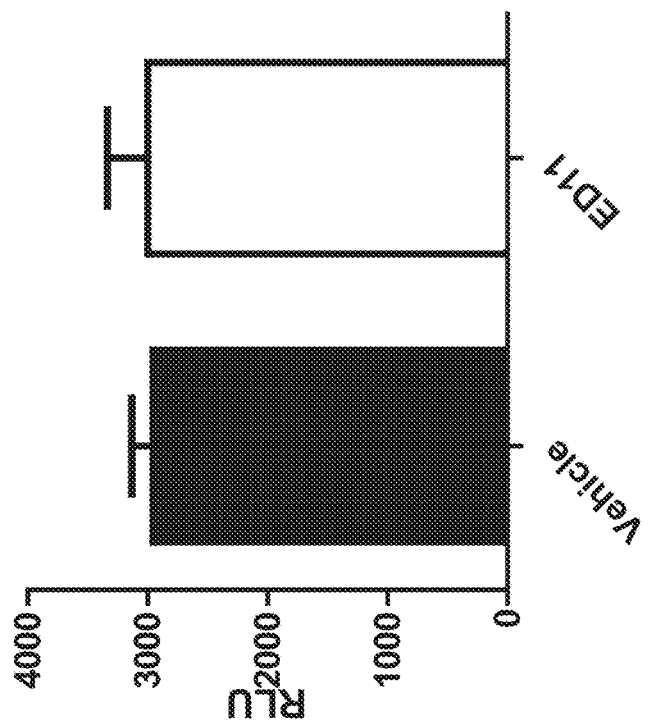
Figure 2C:
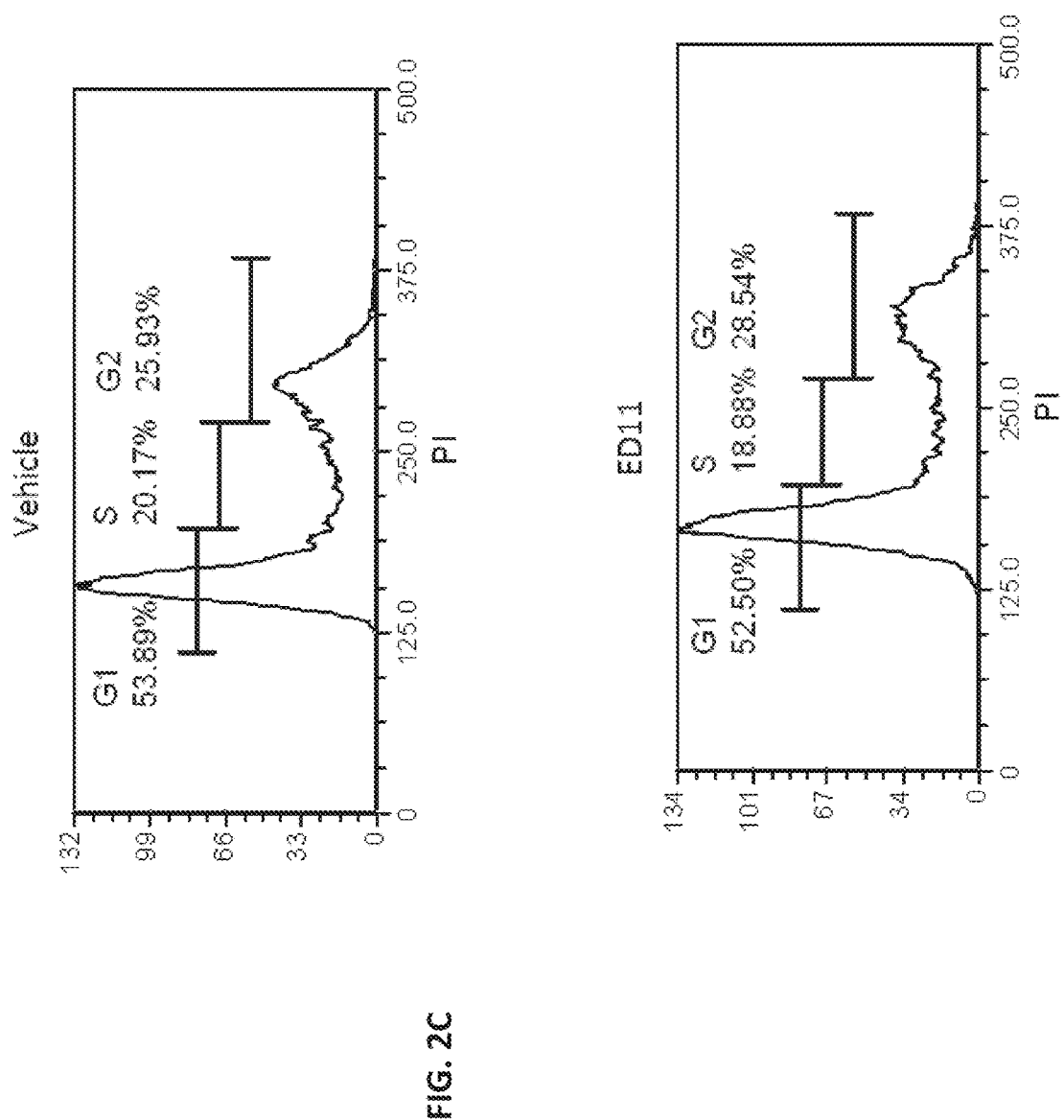
Figure 4D:
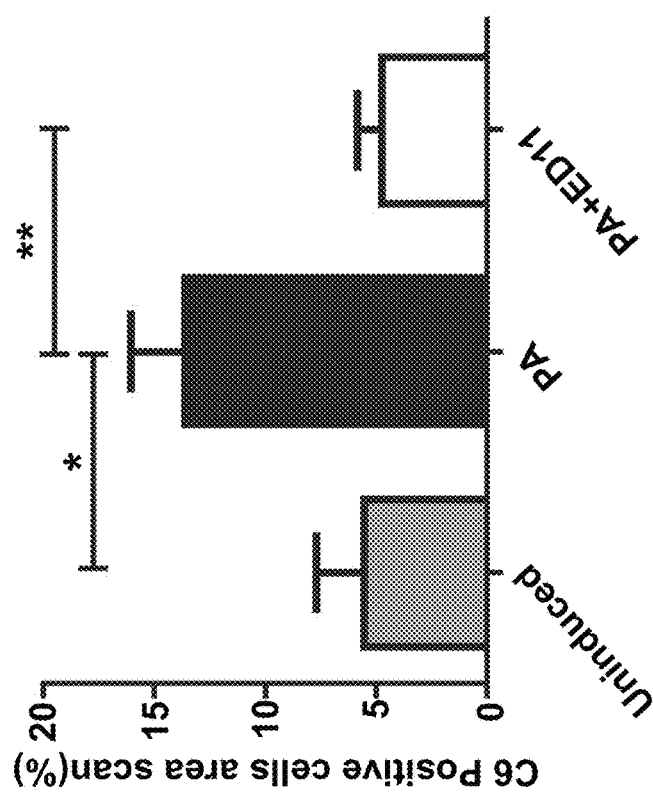

FIGS. 2A-C—ED11 does not influence cell viability, proliferation or cell cycle status in a basal state: A. Cell viability was measured using ALAMAR blue assay after 48 hours incubation with ED11, demonstrating no reduction in cell viability. B. Cell proliferative state was measured using BrdU proliferation assay, indicating no proliferative effect of ED11. C. Cell cycle is not altered as a result of ED11 O.N. incubation.

FIGS. 3A-D—ED11 inhibits in-cell caspase-6 activity following glutamate exposure in SH-SY5Y cells, and protects SH-SY5Y cells viability from glutamate induced toxicity: A-B. Annexin V PI apoptosis assay shows a significant reduction of the apoptotic process caused by glutamate in cells treated with ED11. Graph represents the means of 4 independent experiments. C. Cell viability evaluation as measured by Alamar blue viability assay shows ED11 protects cell viability from glutamate insult. D. Glutamate increases caspase-6 activity as measured by in-cell FLICA caspase-6 activity assay. This increase in caspase-6 activity is highly moderated when cells are pre-treated with ED11. Error bars represent S.E.M. (B) One-way ANOVA, (D) Two-way ANOVA. *P<0.05 **P<0.001.

FIGS. 4A-D—ED11 protects PC12 cells from mutant Huntingtin's toxicity: PC12 cells were induced to express mutant Huntingtin (145Q) by PA and were grown under serum deprivation condition. A. Cell viability was measured by Alamar blue viability assay, 48 and 72 hours post induction, demonstrating that ED11 protects cell viability from mHtt toxicity. B. Cell death measured by LDH release, 48 and 72 hours after mHtt induction, was highly attenuated by ED11. C-D. Representative microscopy pictures (C) and area scan quantification (D) show ED11 inhibits in-cell caspase-6 activity initiated by mHtt. Error bars represents S.E.M. (A-B) Two-way ANOVA, (D) One-way ANOVA. *P<0.05 **P<0.01.

FIGS. 5A-B—ED11 prevents mHtt direct cleavage by caspase-6: BACHD striata protein extracts were incubated with caspase-6 for 20 minutes in 37° C. and proteins were assayed using standard western blot assay. Lane description: 1-2: Wild type control extracts. 3-4: BACHD without C6 control. 5-6: BACHD with C6+DMSO 7-8: BACHD with C6+ED11. A-B. Incubation with Anti-Htt 4-19 antibody (A) or MAB 2166 (B) showed caspase-6 fragmentation of mHtt (*) is blocked in the presence of ED11.

Figure 6:
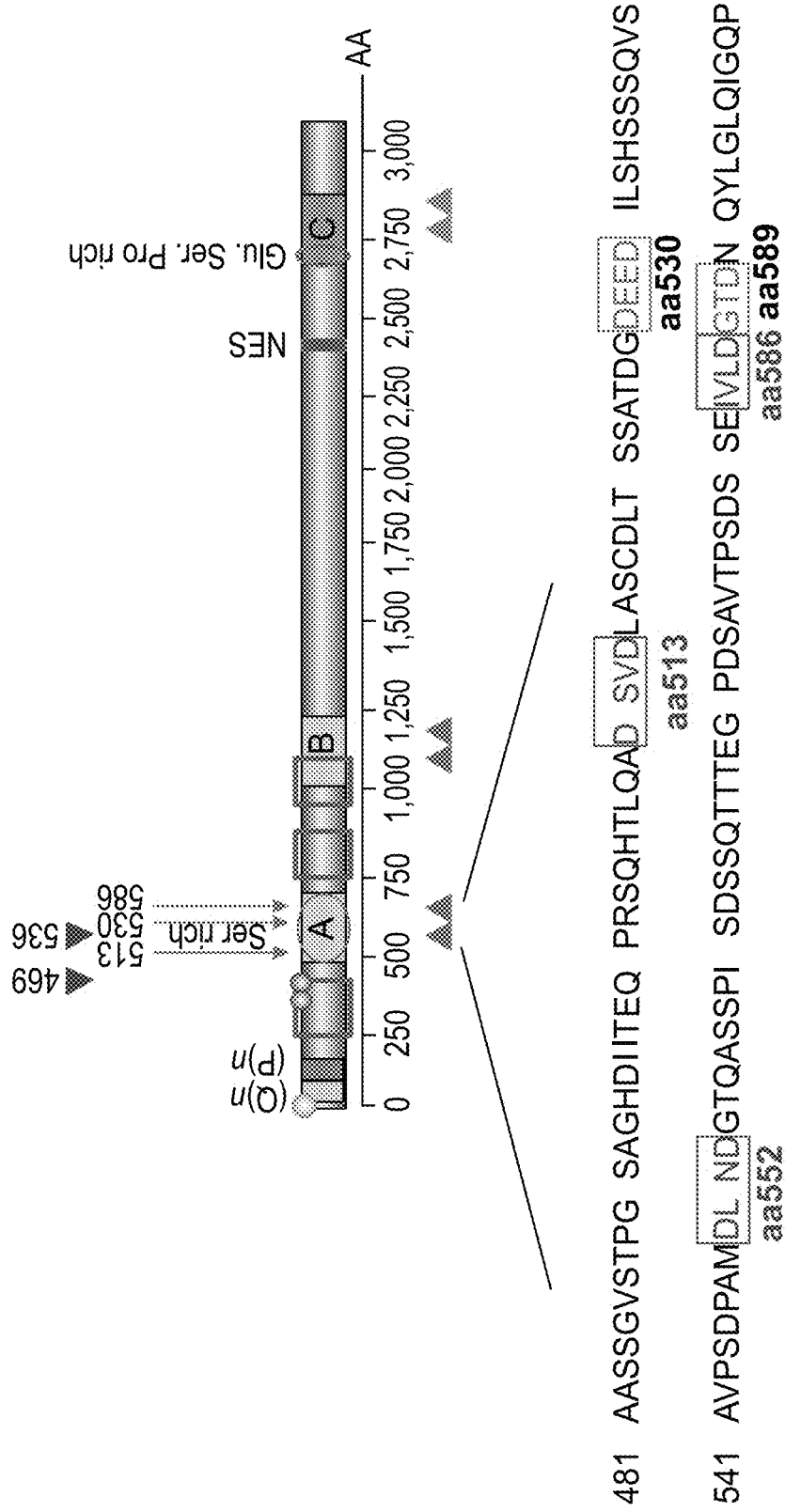

FIG. 6—Huntingtin structure and cleavage sites diagram (modified from Cattaneo et al. Nat Rev Neurosci, 2005, 6, 919-930. (Q)n indicates the polyglutamine tract, which is followed by a polyproline sequence, (P)n. The arrows indicate the caspase cleavage sites and their amino acid positions, and the blue arrowheads the calpain cleavage sites and their amino acid position. Green and orange arrowheads point to the approximate amino acid regions for protease cleavage. NES is the nuclear export signal. Blue lines zoom in the amino acid sequence most relevant for caspase cleavage of HTT (Adapted from Warby et-al., Human Molecular Genetics, 2008, 17, 2390-2404). The illustrated amino acid sequence is set forth in SEQ ID NO: 32.

Figure 7A:
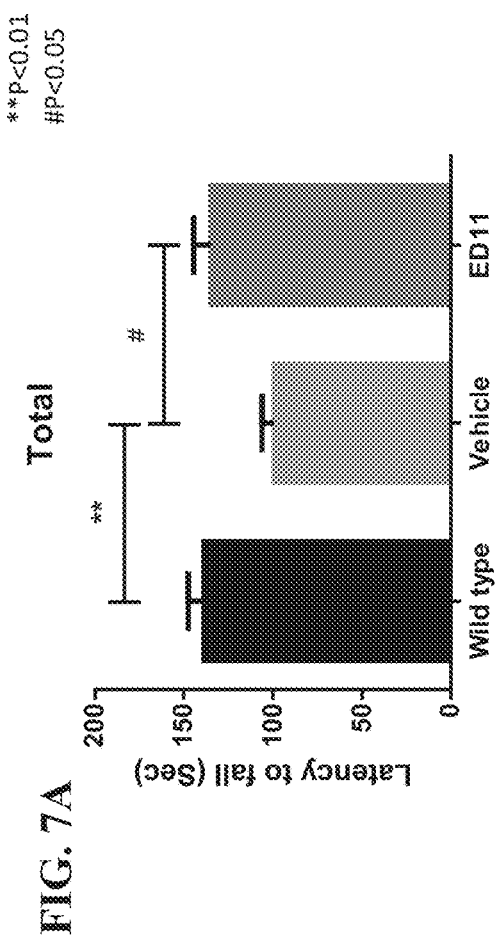
Figure 7C:
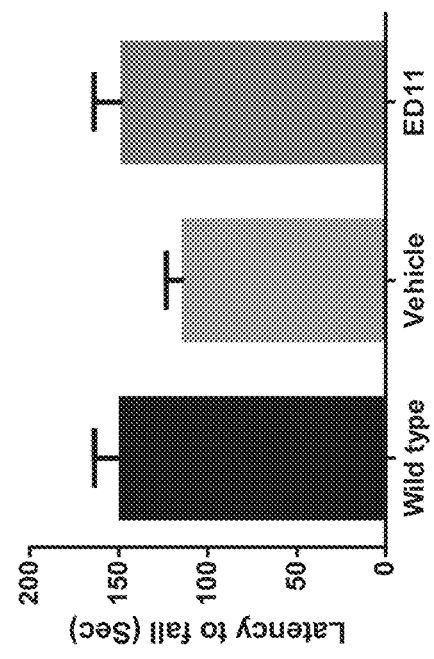
Figure 7B:
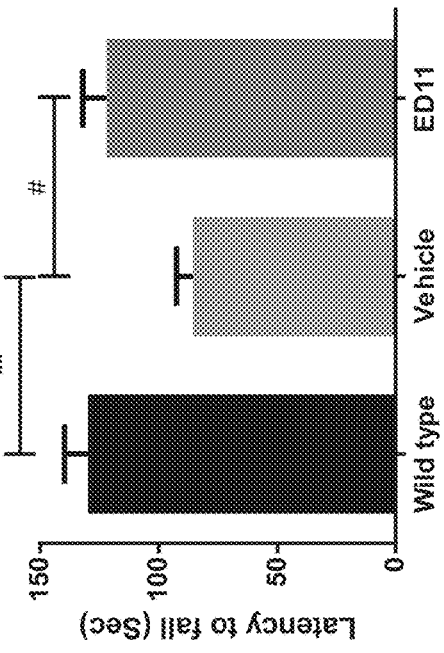

FIGS. 7A-C are bar graphs illustrating that the ED11 peptide protects Huntington's disease mouse model BACHD from motor deterioration as tested in the accelerating Rotarod test.

Figure 8:
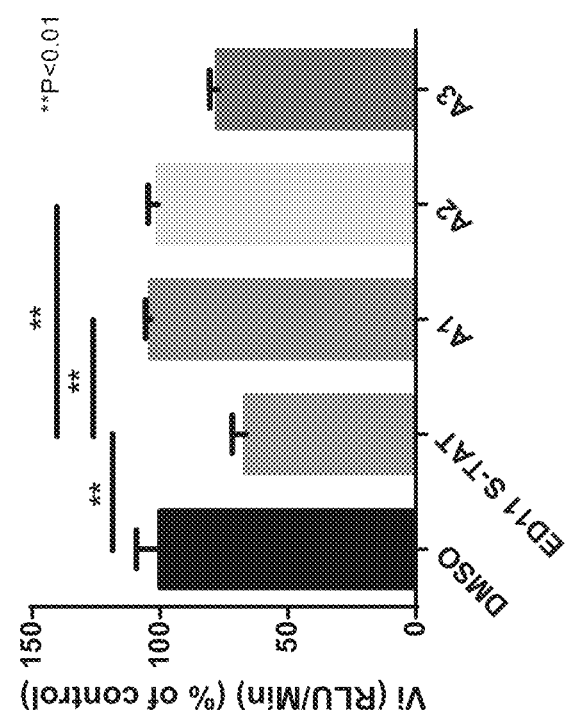

FIG. 8 is a bar graph illustrating that the amino acids at positions X1 and X4 of the ED11 peptide are important for the caspase 6 inhibitory activity.

|  |  |
|---|---|
| ED11 S-TAT: | YGRKKRRSSEIVLDGTDN; (SEQ ID NO: 28) |
| A1: | YGRKKRRSSEAVLDGTDN; (SEQ ID NO: 29) |
| A2: | YGRKKRRSSEIVLAGTDN; (SEQ ID NO: 30) |
| A3: | YGRKKRRSSEIVLDGTAN. (SEQ ID NO: 31) |

DESCRIPTION OF THE PREFERRED EMBODIMENTS

The present invention relates to peptides for the treatment of neurodegenerative disorders and more specifically for the treatment of Huntington's disease (HD).

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Huntington's disease (HD) is an autosomal dominant inherited neurodegenerative disease. It is characterized by the progressive deterioration of cognitive and motor functions, with a fatal outcome after approximately 10-15 years of onset. When the mutated protein huntingtin carries over 40 glutamine repeats at the N-terminal, HD will occur. The precise pathogenic mechanism of mutant Huntingtin is unknown. However, it was shown that caspase-6 plays a key role in the apoptotic events seen in HD. Caspase-6 is activated early in the disease progress, inducing different cellular dysfunctions Importantly, caspase-6 proteolysis of mutant huntingtin is known to be an essential process in generating toxic N-terminal fragments, which leads to neurodegeneration and appearance of disease symptoms. Therefore, inhibiting caspase-6 activity was suggested as a promising therapeutic target for reducing mutant huntingtin toxicity, and rescuing neuronal cells from degeneration.

The present inventors constructed huntingtin cleavage site based peptides fused with a cell penetrating peptide (CPP) to be used as a therapeutic for treating Huntingtin.

The present inventors discovered that a minimum core sequence of 5 amino acids of the caspase cleavage site was required for the peptide to have therapeutic activity. Several candidate peptides comprising this core sequenced were synthesized and tested biochemically. One of the peptides, (ED11), was composed of 11 amino acids (aa) derived from huntingtin sequence fused with 13 aa of the CPP (SEQ ID NO: 6). This peptide significantly and specifically reduced caspase-6 activity as indicated by caspase-6 activity assay in a cell free system (FIGS. 1A-F). Moreover, in neuronal cells this peptide inhibited caspase-6 activity, and protected the cells from glutamate toxicity, an important factor in the pathogenesis of HD (FIGS. 3A-D). Furthermore, in PC12 cells, expressing mutant huntingtin, the peptide markedly reduced the serum deprivation induced toxicity, compared to wild-type PC12 cells (FIGS. 4A-D). Whilst further reducing the present invention to practice, the present inventors demonstrated that when BACHD mice brain striatum extracts were incubated with caspase-6, the addition of the peptide significantly inhibited human mutant huntingtin fragmentation.

In vivo administration of the peptide to BACHD mice had therapeutic effects as assayed by rotarod performance (FIGS. 7A-C). Importantly, the peptide was found to be non-toxic to neuronal cells even at high doses (FIGS. 2A-C).

The present inventors propose the use of the above described peptides for the treatment of caspase 6 related diseases in general and Huntingtin Disease in particular.

Thus, according to one aspect of the present invention there is provided an isolated peptide comprising a Huntingtin (Htt) amino acid sequence being no longer than 15 amino acids, wherein the Htt amino acid sequence comprises the sequence $X_1X_2X_3X_4X_5$ (SEQ ID NO: 34) wherein $X_1$ is a hydrophobic amino acid or threonine, $X_2$ is a hydrophobic amino acid, $X_3$ is a hydrophobic amino acid, $X_4$ is an acidic amino acid and $X_5$ is selected from the group consisting of glycine, serine and alanine, the peptide capable of specifically inhibiting the activity of caspase 6.

The term "peptide" as used herein refers to a polymer of natural or synthetic amino acids, encompassing native peptides (either degradation products, synthetically synthesized polypeptides or recombinant polypeptides) and peptidomimetics (typically, synthetically synthesized peptides), as well as peptoids and semipeptoids which are polypeptide analogs, which may have, for example, modifications rendering the peptides even more stable while in a body or more capable of penetrating into cells.

Such modifications include, but are not limited to N terminus modification, C terminus modification, polypeptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Polypeptide bonds (—CO—NH—) within the polypeptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), polypeptide derivatives (—N(R)—CH2-CO—), wherein R is the "normal" side chain, naturally presented on the carbon atom.

These modifications can occur at any of the bonds along the polypeptide chain and even at several (2-3) at the same time.

Natural aromatic amino acids, Trp, Tyr and Phe, may be substituted for synthetic non-natural acid such as Phenylglycine, TIC, naphthylelanine (Nol), ring-methylated derivatives of Phe, halogenated derivatives of Phe or o-methyl-Tyr.

In addition to the above, the polypeptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids (stereoisomers).

Tables 1 and 2 below list naturally occurring amino acids (Table 1) and non-conventional or modified amino acids (Table 2) which can be used with the present invention.

TABLE 1

| Amino Acid | Three-Letter Abbreviation | One-letter Symbol |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE 2

| Non-conventional amino acid | Code | Non-conventional amino acid | Code |
| --- | --- | --- | --- |
| ornithine | Orn | hydroxyproline | Hyp |
| α-aminobutyric acid | Abu | aminonorbornyl-carboxylate | Norb |
| D-alanine | Dala | aminocyclopropane-carboxylate | Cpro |
| D-arginine | Darg | N-(3-guanidinopropyl)glycine | Narg |
| D-asparagine | Dasn | N-(carbamylmethyl)glycine | Nasn |
| D-aspartic acid | Dasp | N-(carboxymethyl)glycine | Nasp |
| D-cysteine | Dcys | N-(thiomethyl)glycine | Ncys |
| D-glutamine | Dgln | N-(2-carbamylethyl)glycine | Ngln |
| D-glutamic acid | Dglu | N-(2-carboxyethyl)glycine | Nglu |
| D-histidine | Dhis | N-(imidazolylethyl)glycine | Nhis |
| D-isoleucine | Dile | N-(1-methylpropyl)glycine | Nile |
| D-leucine | Dleu | N-(2-methylpropyl)glycine | Nleu |
| D-lysine | Dlys | N-(4-aminobutyl)glycine | Nlys |
| D-methionine | Dmet | N-(2-methylthioethyl)glycine | Nmet |
| D-ornithine | Dorn | N-(3-aminopropyl)glycine | Norn |
| D-phenylalanine | Dphe | N-benzylglycine | Nphe |
| D-proline | Dpro | N-(hydroxymethyl)glycine | Nser |
| D-serine | Dser | N-(1-hydroxyethyl)glycine | Nthr |
| D-threonine | Dthr | N-(3-indolylethyl) glycine | Nhtrp |
| D-tryptophan | Dtrp | N-(p-hydroxyphenyl)glycine | Ntyr |
| D-tyrosine | Dtyr | N-(1-methylethyl)glycine | Nval |
| D-valine | Dval | N-methylglycine | Nmgly |
| D-N-methylalanine | Dnmala | L-N-methylalanine | Nmala |
| D-N-methylarginine | Dnmarg | L-N-methylarginine | Nmarg |

TABLE 2-continued

| Non-conventional amino acid | Code | Non-conventional amino acid | Code |
|---|---|---|---|
| D-N-methylasparagine | Dnmasn | L-N-methylasparagine | Nmasn |
| D-N-methylasparatate | Dnmasp | L-N-methylaspartic acid | Nmasp |
| D-N-methylcysteine | Dnmcys | L-N-methylcysteine | Nmcys |
| D-N-methylglutamine | Dnmgln | L-N-methylglutamine | Nmgln |
| D-N-methylglutamate | Dnmglu | L-N-methylglutamic acid | Nmglu |
| D-N-methylhistidine | Dnmhis | L-N-methylhistidine | Nmhis |
| D-N-methylisoleucine | Dnmile | L-N-methylisolleucine | Nmile |
| D-N-methylleucine | Dnmleu | L-N-methylleucine | Nmleu |
| D-N-methyllysine | Dnmlys | L-N-methyllysine | Nmlys |
| D-N-methylmethionine | Dnmmet | L-N-methylmethionine | Nmmet |
| D-N-methylornithine | Dnmorn | L-N-methylornithine | Nmorn |
| D-N-methylphenylalanine | Dnmphe | L-N-methylphenylalanine | Nmphe |
| D-N-methylproline | Dnmpro | L-N-methylproline | Nmpro |
| D-N-methylserine | Dnmser | L-N-methylserine | Nmser |
| D-N-methylthreonine | Dnmthr | L-N-methylthreonine | Nmthr |
| D-N-methyltryptophan | Dnmtrp | L-N-methyltryptophan | Nmtrp |
| D-N-methyltyrosine | Dnmtyr | L-N-methyltyrosine | Nmtyr |
| D-N-methylvaline | Dnmval | L-N-methylvaline | Nmval |
| L-norleucine | Nle | L-N-methylnorleucine | Nmnle |
| L-norvaline | Nva | L-N-methylnorvaline | Nmnva |
| L-ethylglycine | Etg | L-N-methyl-ethylglycine | Nmetg |
| L-t-butylglycine | Tbug | L-N-methyl-t-butylglycine | Nmtbug |
| L-homophenylalanine | Hphe | L-N-methyl-homophenylalanine | Nmhphe |
| α-naphthylalanine | Anap | N-methyl-α-naphthylalanine | Nmanap |
| penicillamine | Pen | N-methylpenicillamine | Nmpen |
| γ-aminobutyric acid | Gabu | N-methyl-γ-aminobutyrate | Nmgabu |
| cyclohexylalanine | Chexa | N-methyl-cyclohexylalanine | Nmchexa |
| cyclopentylalanine | Cpen | N-methyl-cyclopentylalanine | Nmcpen |
| α-amino-α-methylbutyrate | Aabu | N-methyl-α-amino-α-methylbutyrate | Nmaabu |
| α-aminoisobutyric acid | Aib | N-methyl-α-aminoisobutyrate | Nmaib |
| D-α-methylarginine | Dmarg | L-α-methylarginine | Marg |
| D-α-methylasparagine | Dmasn | L-α-methylasparagine | Masn |
| D-α-methylaspartate | Dmasp | L-α-methylaspartate | Masp |
| D-α-methylcysteine | Dmcys | L-α-methylcysteine | Mcys |
| D-α-methylglutamine | Dmgln | L-α-methylglutamine | Mgln |
| D-α-methyl glutamic acid | Dmglu | L-α-methylglutamate | Mglu |
| D-α-methylhistidine | Dmhis | L-α-methylhistidine | Mhis |
| D-α-methylisoleucine | Dmile | L-α-methylisoleucine | Mile |
| D-α-methylleucine | Dmleu | L-α-methylleucine | Mleu |
| D-α-methyllysine | Dmlys | L-α-methyllysine | Mlys |
| D-α-methylmethionine | Dmmet | L-α-methylmethionine | Mmet |
| D-α-methylornithine | Dmorn | L-α-methylornithine | Morn |
| D-α-methylphenylalanine | Dmphe | L-α-methylphenylalanine | Mphe |
| D-α-methylproline | Dmpro | L-α-methylproline | Mpro |
| D-α-methylserine | Dmser | L-α-methylserine | Mser |
| D-α-methylthreonine | Dmthr | L-α-methylthreonine | Mthr |
| D-α-methyltryptophan | Dmtrp | L-α-methyltryptophan | Mtrp |
| D-α-methyltyrosine | Dmtyr | L-α-methyltyrosine | Mtyr |
| D-α-methylvaline | Dmval | L-α-methylvaline | Mval |
| N-cyclobutylglycine | Ncbut | L-α-methylnorvaline | Mnva |
| N-cycloheptylglycine | Nchep | L-α-methylethylglycine | Metg |
| N-cyclohexylglycine | Nchex | L-α-methyl-t-butylglycine | Mtbug |
| N-cyclodecylglycine | Ncdec | L-α-methyl-homophenylalanine | Mhphe |
| N-cyclododecylglycine | Ncdod | α-methyl-α-naphthylalanine | Manap |
| N-cyclooctylglycine | Ncoct | α-methylpenicillamine | Mpen |
| N-cyclopropylglycine | Ncpro | α-methyl-γ-aminobutyrate | Mgabu |
| N-cycloundecylglycine | Ncund | α-methyl-cyclohexylalanine | Mchexa |
| N-(2-aminoethyl)glycine | Naeg | α-methyl-cyclopentylalanine | Mcpen |
| N-(2,2-diphenylethyl)glycine | Nbhm | N-(N-(2,2-diphenylethyl) carbamylmethyl-glycine | Nnbhm |
| N-(3,3-diphenylpropyl)glycine | Nbhe | N-(N-(3,3-diphenylpropyl) carbamylmethyl-glycine | Nnbhe |
| 1-carboxy-1-(2,2-diphenyl-ethylamino)cyclopropane | Nmbc | 1,2,3,4-tetrahydroisoquinoline-3-carboxylic acid | Tic |
| phosphoserine | pSer | phosphothreonine | pThr |
| phosphotyrosine | pTyr | O-methyl-tyrosine | |
| 2-aminoadipic acid | | hydroxylysine | |

The amino acids of the peptides of the present invention may be substituted either conservatively or non-conservatively.

The term "conservative substitution" as used herein, refers to the replacement of an amino acid present in the native sequence in the peptide with a naturally or non-naturally occurring amino or a peptidomimetics having similar steric properties. Where the side-chain of the native amino acid to be replaced is either polar or hydrophobic, the conservative substitution should be with a naturally occurring amino acid, a non-naturally occurring amino acid or with a peptidomimetic moiety which is also polar or hydrophobic (in addition to having the same steric properties as the side-chain of the replaced amino acid).

As naturally occurring amino acids are typically grouped according to their properties, conservative substitutions by naturally occurring amino acids can be easily determined bearing in mind the fact that in accordance with the invention replacement of charged amino acids by sterically similar non-charged amino acids are considered as conservative substitutions.

For producing conservative substitutions by non-naturally occurring amino acids it is also possible to use amino acid analogs (synthetic amino acids) well known in the art. A peptidomimetic of the naturally occurring amino acid is well documented in the literature known to the skilled practitioner.

When affecting conservative substitutions the substituting amino acid should have the same or a similar functional group in the side chain as the original amino acid.

The phrase "non-conservative substitutions" as used herein refers to replacement of the amino acid as present in the parent sequence by another naturally or non-naturally occurring amino acid, having different electrochemical and/or steric properties. Thus, to the side chain of the substituting amino acid can be significantly larger (or smaller) than the side chain of the native amino acid being substituted and/or can have functional groups with significantly different electronic properties than the amino acid being substituted. Examples of non-conservative substitutions of this type include the substitution of phenylalanine or cycohexylmethyl glycine for alanine, isoleucine for glycine, or —NH—CH[(—CH$_2$)$_5$—COOH]—CO— for aspartic acid. Those non-conservative substitutions which fall under the scope of the present invention are those which still constitute a peptide having anti-bacterial properties.

As mentioned, the N and C termini of the peptides of the present invention may be protected by function groups. Suitable functional groups are described in Green and Wuts, "Protecting Groups in Organic Synthesis", John Wiley and Sons, Chapters 5 and 7, 1991, the teachings of which are incorporated herein by reference. Preferred protecting groups are those that facilitate transport of the compound attached thereto into a cell, for example, by reducing the hydrophilicity and increasing the lipophilicity of the compounds.

These moieties can be cleaved in vivo, either by hydrolysis or enzymatically, inside the cell. Hydroxyl protecting groups include esters, carbonates and carbamate protecting groups. Amine protecting groups include alkoxy and aryloxy carbonyl groups, as described above for N-terminal protecting groups. Carboxylic acid protecting groups include aliphatic, benzylic and aryl esters, as described above for C-terminal protecting groups. In one embodiment, the carboxylic acid group in the side chain of one or more glutamic acid or aspartic acid residue in a peptide of the present invention is protected, preferably with a methyl, ethyl, benzyl or substituted benzyl ester.

Examples of N-terminal protecting groups include acyl groups (—CO—R1) and alkoxy carbonyl or aryloxy carbonyl groups (—CO—O—R1), wherein R1 is an aliphatic, substituted aliphatic, benzyl, substituted benzyl, aromatic or a substituted aromatic group. Specific examples of acyl groups include acetyl, (ethyl)-CO—, n-propyl-CO—, iso-propyl-CO—, n-butyl-CO—, sec-butyl-CO—, t-butyl-CO—, hexyl, lauroyl, palmitoyl, myristoyl, stearyl, oleoyl phenyl-CO—, substituted phenyl-CO—, benzyl-CO— and (substituted benzyl)-CO—. Examples of alkoxy carbonyl and aryloxy carbonyl groups include CH3-O—CO—, (ethyl)-O—CO—, n-propyl-O—CO—, iso-propyl-O—CO—, n-butyl-O—CO—, sec-butyl-O—CO—, t-butyl-O—CO—, phenyl-O—CO—, substituted phenyl-O—CO— and to benzyl-O—CO—, (substituted benzyl)-O—CO—. Adamantan, naphtalen, myristoleyl, tuluen, biphenyl, cinnamoyl, nitrobenzoy, toluoyl, furoyl, benzoyl, cyclohexane, norbomane, Z-caproic. In order to facilitate the N-acylation, one to four glycine residues can be present in the N-terminus of the molecule.

The carboxyl group at the C-terminus of the compound can be protected, for example, by an amide (i.e., the hydroxyl group at the C-terminus is replaced with —NH$_2$, —NHR$_2$ and —NR$_2$R$_3$) or ester (i.e. the hydroxyl group at the C-terminus is replaced with —OR$_2$). R$_2$ and R$_3$ are independently an aliphatic, substituted aliphatic, benzyl, substituted benzyl, aryl or a substituted aryl group. In addition, taken together with the nitrogen atom, R$_2$ and R$_3$ can form a C4 to C8 heterocyclic ring with from about 0-2 additional heteroatoms such as nitrogen, oxygen or sulfur. Examples of suitable heterocyclic rings include piperidinyl, pyrrolidinyl, morpholino, thiomorpholino or piperazinyl. Examples of C-terminal protecting groups include —NH$_2$, —NHCH$_3$, —N(CH$_3$)$_2$, —NH(ethyl), —N(ethyl)$_2$, —N(methyl) (ethyl), —NH(benzyl), —N(C1-C4 alkyl) (benzyl), —NH(phenyl), —N(C1-C4 alkyl) (phenyl), —OCH$_3$, —O-(ethyl), —O-(n-propyl), —O-(n-butyl), —O-(iso-propyl), —O-(sec-butyl), —O-(t-butyl), —O-benzyl and —O-phenyl.

The peptides of the present invention may also comprise non-amino acid moieties, such as for example, hydrophobic moieties (various linear, branched, cyclic, polycyclic or hetrocyclic hydrocarbons and hydrocarbon derivatives) attached to the peptides; non-peptide penetrating agents; various protecting groups, especially where the compound is linear, which are attached to the compound's terminals to decrease degradation. Chemical (non-amino acid) groups present in the compound may be included in order to improve various physiological properties such; decreased degradation or clearance; decreased repulsion by various cellular pumps, improve immunogenic activities, improve various modes of administration (such as attachment of various sequences which allow penetration through various barriers, through the gut, etc.); increased specificity, increased affinity, decreased toxicity and the like.

Attaching the amino acid sequence component of the peptides of the invention to other non-amino acid agents may be by covalent linking, by non-covalent complexion, for example, by complexion to a hydrophobic polymer, which can be degraded or cleaved producing a compound capable of sustained release; by entrapping the amino acid part of to the peptide in liposomes or micelles to produce the final peptide of the invention. The association may be by the entrapment of the amino acid sequence within the other component (liposome, micelle) or the impregnation of the amino acid sequence within a polymer to produce the final peptide of the invention.

The peptides of the invention may be linear or cyclic (cyclization may improve stability). Cyclization may take place by any means known in the art. Where the compound is composed predominantly of amino acids, cyclization may be via N- to C-terminal, N-terminal to side chain and N-terminal to backbone, C-terminal to side chain, C-terminal to backbone, side chain to backbone and side chain to side chain, as well as backbone to backbone cyclization. Cyclization of the peptide may also take place through non-amino acid organic moieties comprised in the peptide.

The peptides of the present invention can be biochemically synthesized such as by using standard solid phase techniques. These methods include exclusive solid phase synthesis, partial solid phase synthesis methods, fragment condensation, classical solution synthesis. Solid phase polypeptide synthesis procedures are well known in the art and further described by John Morrow Stewart and Janis Dillaha Young, Solid Phase Polypeptide Syntheses (2nd Ed., Pierce Chemical Company, 1984).

Large scale peptide synthesis is described by Andersson Biopolymers 2000; 55(3):227-50.

Synthetic peptides can be purified by preparative high performance liquid chromatography [Creighton T. (1983) Proteins, structures and molecular principles. WH Freeman and Co. N.Y.] and the composition of which can be confirmed via amino acid sequencing.

Recombinant techniques may also be used to generate the peptides of the present invention. To produce a peptide of the present invention using recombinant technology, a polynucleotide encoding the peptide of the present invention is ligated into a nucleic acid expression vector, which comprises the polynucleotide sequence under the transcriptional control of a cis-regulatory sequence (e.g., promoter sequence) suitable for directing constitutive, tissue specific or inducible transcription of the polypeptides of the present invention in the host cells.

In addition to being synthesizable in host cells, the peptides of the present invention can also be synthesized using in vitro expression systems. These methods are to well known in the art and the components of the system are commercially available.

Peptides contemplated by the present invention comprise the core sequence IVLD—SEQ ID NO: 1.

Examples of such peptides include:

```
IVLDGTDN;      (SEQ ID NO: 2)

IVLDGTD;       (SEQ ID NO: 3)

IVLDGT;        (SEQ ID NO: 4)

IVLDG;         (SEQ ID NO: 5)
```

For the peptide having the sequence as set forth in SEQ ID NO: 2, amino acid "I" may be considered to be in position 1; amino acid "V" may be considered to be in position 2; "amino acid "L" may be considered to be in position 3; "amino acid "D" may be considered to be in position 4; amino acid "G" may be considered to be in position 5; amino acid "T" may be considered to be in position 6; amino acid "D" may be considered to be in position 7; and amino acid "N" may be considered to be in position 8.

Contemplated replacements for any of the amino acids in this sequence include:
1. The use of Valine (V) as a replacement for Iso-leucine (I) at position #1;
2. The use of Threonine (T) as a replacement for Iso-leucine (I) at position #1;
3. The use of Leucine (L) as a replacement for Iso-leucine (I) at position #1;
4. The use of Glutamic acid (E) as a replacement for Aspartic acid (D) at position #4;
5. The use of Serine (S) as a replacement of Glycine(G) at position #5;
The use of Alanine(A) as a replacement of Glycine(G) at position #5; or
6. The use of Glutamic acid (E) as a replacement for Aspartic acid (D) at position #7.

Additional contemplated replacements for any of the amino acids in this sequence include:
1. The use of Alanine (A) as a replacement for Iso-leucine (I) at position #1;
2. The use of Methionine (M) as a replacement for Iso-leucine (I) at position #1;
3. The use of Phenylalanine (F) as a replacement for Iso-leucine (I) at position #1;
4. The use of Tyrosine (Y) as a replacement for Iso-leucine (I) at position #1;
5. The use of Tryptopane (W) as a replacement for Iso-leucine (I) at position #1;
6. The use of Leucine (L) as a replacement for Valine (V) at position #2;
7. The use of Iso-Leucine (I) as a replacement for Valine (V) at position #2;
8. The use of Alanine (A) as a replacement for Valine (V) at position #2;
9. The use of Methionine (M) as a replacement for Valine (V) at position #2;
10. The use of Phenylalanine (F) as a replacement for Valine (V) at position #2;
11. The use of Tyrosine (Y) as a replacement for Valine (V) at position #2;
12. The use of Tryptopane (W) as a replacement for Valine (V) at position #2;
13. The use of Valine (V) as a replacement for Leucine (L) at position #3;
14. The use of Iso-Leucine (I) as a replacement for Leucine (L) at position #3;
15. The use of Alanine (A) as a replacement for Leucine (L) at position #3;
16. The use of Methionine (M) as a replacement for Leucine (L) at position #3;
17. The use of Phenylalanine (F) as a replacement for Leucine (L) at position #3;
18. The use of Tyrosine (Y) as a replacement for Leucine (L) at position #3;
19. The use of Tryptopane (W) as a replacement for Leucine (L) at position #3;
20. The use of Serine (S) as a replacement for Threonine (T) at position #6;
21. The use of Aspargine (N) as a replacement for Threonine (T) at position #6;
22. The use of Glutamine (Q) as a replacement for Threonine (T) at position #6;
23. The use of Serine (S) as a replacement for Aspargine (N) at position #8;
24. The use of Threonine (T) as a replacement for Aspargine (N) at position #8;
25. The use of Glutamine (Q) as a replacement for Aspargine (N) at position #8; or
26. D-confirmation of Aspartic acid (D) at position #4 of the core peptide.

As mentioned, the peptides of this aspect of the present invention comprise a caspase 6 inhibitory activity. Methods of analyzing whether a peptide comprises caspase 6 inhibitory activity are known in the art and include use of commercial kits such as those available from Promega (catalogue number G0970), Abcom (catalogue number ab39707) and Millipore (catalogue number APT168).

Preferably, the peptides inhibit the activity of caspase 6 to a greater extent than they inhibit the activity of caspase 3. For example the Ki of the peptide may be at least 2 fold, preferably at least 5 fold lower for caspase 6 than for caspase 3. Methods of determining the inhibitory activity of the peptides towards caspase 3 are known in the to art and include the use of kits such as those available from Promega, Cell Signal or Sigma.

As mentioned, the Huntingtin (Htt) amino acid sequence is preferably no longer than 15 amino acids, more preferably no longer than 14 amino acids, more preferably no longer than 13 amino acids, more preferably no longer than 12 amino acids, more preferably no longer than 11 amino acids.

According to another embodiment, the Htt amino acid sequence is no longer than 10 amino acids, more preferably no longer than 9 amino acids, more preferably no longer than 8 amino acids.

As mentioned, the peptides described herein may be attached to a cell penetrating agent.

As used herein the phrase "penetrating agent" refers to an agent which enhances translocation of any of the attached peptide across a cell membrane.

According to one embodiment, the penetrating agent is a peptide and is attached to the Huntingtin related peptide (either directly or non-directly) via a peptide bond.

Typically, peptide penetrating agents have an amino acid composition containing either a high relative abundance of positively charged amino acids such as lysine or arginine, or have sequences that contain an alternating pattern of polar/charged amino acids and non-polar, hydrophobic amino acids.

Examples of peptide penetrating agents include long and short versions of TAT (YGRKKRR—SEQ ID NO: 14 and YGRKKRRQRRR—SEQ ID NO: 15) and PTD (RRQRR—SEQ ID NO: 16. By way of non-limiting example, cell penetrating peptide (CPP) sequences may be used in order to enhance intracellular penetration. CPPs may include:

```
GRKKRRQRRRPPQ-;        SEQ ID NO: 7

GRKKRRQRRRPP-;         SEQ ID NO: 8

GRKKRRQRRRP-;          SEQ ID NO: 9

GRKKRRQRRR-;           SEQ ID NO: 10

GRKKRRQRR-;            SEQ ID NO: 11

GRKKRRQR-;             SEQ ID NO: 12

GRKKRRQ-;              SEQ ID NO: 13

YGRKKRR-;              SEQ ID NO: 14

YGRKKRRQRRR-;          SEQ ID NO: 15

RRQRR-.                SEQ ID NO: 16
```

According to a particular embodiment, the Htt peptides are attached to the cell penetrating peptides via a linking moiety.

Examples of linking moieties include but are not limited to a simple covalent bond, a flexible peptide linker, a disulfide bridge or a polymer such as polyethylene glycol (PEG). Peptide linkers may be entirely artificial (e.g., comprising 2 to 20 amino acid residues independently selected from the group consisting of glycine, serine, asparagine, threonine and alanine) or adopted from naturally occurring proteins. Disulfide bridge formation can be achieved, e.g., by addition of cysteine residues, as further described herein below.

Selection of the link between the two peptides should take into account that the link should not substantially interfere with the ability of the Htt peptide to inhibit caspase 6 activity or the ability of the cell penetrating peptide to traverse the cell membrane.

Thus, for example, the linking moiety is optionally a moiety which is covalently attached to a side chain, an N-terminus or a C-terminus of the Htt peptide, as well as to a side chain, an N-terminus or a C-terminus of the cell penetrating peptide.

The linking moiety may be attached to the C-terminus of the Htt peptide monomer and to the N-terminus of the cell penetrating peptide.

Alternatively, the linking moiety may be attached to the N-terminus of the Htt peptide monomer and to the C-terminus of the cell penetrating peptide.

The linking moiety (or linking peptide) may comprise additional amino acids from the huntingtin protein.

Thus, according to a particular embodiment, the linking moiety comprises the sequence SSE.

The linker may comprise additional amino acids linked together by peptide bonds which serve as spacers such that the linker does not interfere with the biological activity of the final compound. The linker is preferably made up of amino acids linked together by peptide bonds. Thus, in preferred embodiments, the linker is made up of from 1 to 10 amino acids linked by peptide bonds, wherein the amino acids are selected to from the 20 naturally occurring amino acids. Some of these amino acids may be glycosylated, as is well understood by those in the art.

In a more preferred embodiment, besides serine and glutamic acid the amino acids in the linker are selected from glycine, alanine, proline, asparagine and lysine. Even more preferably, besides serine and glutamic acid, the linker is made up of a majority of amino acids that are sterically unhindered, such as glycine and alanine.

According to another embodiment, the linking peptide comprises a disulfide bridge.

Thus, in some embodiments of the invention, each of the peptides comprises an amino acid sequence as described herein above and further comprise at least one cysteine residue, such that the peptides are covalently linked to one another via a disulfide bridge formed between a cysteine residue in one peptide and a cysteine residue in another peptide.

Hereinthroughout, the phrases "disulfide bridge" and "disulfide bond" are used interchangeably, and describe a —S—S— bond.

Examples of peptides which include both the Htt sequence and the cell penetrating peptide are disclosed below:

```
GRKKRRQRRRPPQSSEIVLDGTDN-;    SEQ ID NO: 6

GRKKRRQRRRPPQSSEIVLDGTD-;     SEQ ID NO: 17

GRKKRRQRRRPPQSSEIVLDGT-;      SEQ ID NO: 18

GRKKRRQRRRP PQSSEIVLDG-;      SEQ ID NO: 19

GRKKRRQRRRPPQSSEIVLD-;        SEQ ID NO: 20

GRKKRRQRRRPPQIVLDGTDN-;       SEQ ID NO: 21

GRKKRRQRRRPPSSEIVLDGTDN-;     SEQ ID NO: 22

GRKKRRQRRRPSSEIVLDGTDN-;      SEQ ID NO: 23

GRKKRRQRRRSSEIVLDGTDN-;       SEQ ID NO: 24
```

```
-continued
GRKKRRQRRSSEIVLDGTDN-;          SEQ ID NO: 25

GRKKRRQRSSEIVLDGTDN-;           SEQ ID NO: 26

GRKKRRQSSEIVLDGTDN-;            SEQ ID NO: 27
```

The full length peptide (i.e. Huntington peptide, optional linking peptide and optional cell penetrating peptide) is typically no longer than 20 amino acids, 21 amino acids, 22 amino acids, 23 amino acids, 24 amino acids, 25 amino acids, 26 amino acids, to 27 amino acids, 28 amino acids, 29 amino acids or 30 amino acids.

Since the peptides disclosed herein are capable of inhibiting caspase 6, the present inventors propose that they may be used to treat and/or prevent caspase 6 associated diseases, examples of which are provided herein below.

1. chronic degenerative diseases e.g. neurodegenerative disease including Alzheimer's disease, Huntington's' disease, Parkinson's' disease, Multiple sclerosis, amyotrophic lateral sclerosis, spinobulbar atrophy, prion disease, dementia 2. epilepsy or epilepstogenes 3. apoptosis during spinal cord injury 4. apoptosis resulting from traumatic brain injury, or to provide neuroprotective effect, or to provide cerebroprotective effect, 5. treat cytotoxic T cell and natural killer cell-mediated apoptosis associated with autoimmune disease and transplant rejection, 6. to prevent cell death of cardiac cells including heart failure, cardiomyopathy, viral infection or bacterial infection of heart, myocardial ischemia, myocardial infarct, and myocardial ischemia, coronary artery by-pass graft, 7. prevent and/or treat mitochondrial drug toxicity e.g. as a result of chemotherapy or HIV therapy, 8. prevent cell death during viral infection or bacterial infection, 9. prevent and/or treat inflammation or inflammatory diseases, inflammatory bowel disease, sepsis and septic shock, 10. to prevent cell death from follicule to ovocyte stages, from ovocyte to mature egg stages (Nutt et al. 2005; Bergeron et al., 1998); and sperm (for example, methods of freezing and transplanting ovarian tissue, artificial fecondation), or to preserve fertility in women and men after chemotherapy, or to preserve fertility in females and males animals, 11. to prevent and/or treat, macular degenerescence and glaucoma, 12. to prevent and/or treat acute hepatitis, chronic active hepatitis, hepatitis-B, and hepatitis-C, 13. to prevent hair loss, and the hair loss due-to male-pattern baldness, radiation, chemotherapy or emotional stress, 14. to treat or ameliorate skin damage (due to exposure to high level of radiation, heat, burns, chemicals, sun, and autoimmune diseases), 15. to prevent cell death of bone marrow cells in myelodysplastic symdromes, or to treat pancreatisis, or to treat respiratory syndrome, 16. to treat and/or prevent death of gastrointestinal lining epithelial cells, 17. to treat osteoarthitis, rheumatoid arthritis, psoriasis, glomerulonephritis, atherosclerosis, and graft versus host disease, 18. to treat retinal pericyte apoptosis, retinal neurons apoptosis, glaucoma, retinal damages, macular degeneration resulting from ischemia, diabetic retinopaty, or other trauma.

According to a particular embodiment, the disease is a neurodegenerative disease.

Exemplary neurodegenerative diseases include, but are not limited to Huntington's Disease (HD), Alzheimer's Disease (AD), aging and stroke.

Additional neurodegenerative diseases include Parkinson's disease, Multiple Sclerosis, ALS, multi-system atrophy, progressive supranuclear palsy, fronto-temporal dementia with Parkinsonism linked to chromosome 17 and Pick's disease.

The peptides of the present invention may be provided per se or as part of a pharmaceutical composition, where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the caspase 6 inhibitory peptides accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. to Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of to the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (caspase-6 inhibitory peptides) effective to prevent, alleviate or ameliorate symptoms of a disorder (e.g., Huntington's Disease) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to brain or blood to levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Peptide Synthesis and Dissolvent:

ED11 (GRKKRRQRRRPPQSSEIVLDGTDN—SEQ ID NO: 6) and TAT-only (GRKKRRQRRRPPQ—SEQ ID NO: 7) were synthesized by China-Peptides Ltd. with a purification level at over 95%. For the purified caspase activity assays, peptides were dissolved in DMSO. For the cell culture involved experiments, peptides were initially dissolved in cell-culture grade $H_2O$ and further diluted by phosphate-buffered saline (PBS) to the desired concentrations.

Purified Caspase Inhibition Assays:

For determining ED11 caspase-6 inhibition ability, the Caspase-Glo® 6 assay (Promega) was carried out according to the manufacturer's instructions. Briefly, 0.1 U/ml Purified caspase-6 (Enzo life-science) was incubated with 0-12 μM Z-VEID-aminoluciferin in the presence of 10 μM ED11 or DMSO as vehicle control, and luminescent signal of released aminoluciferin (as RLU) was detected using Synergy HT multi-mode micro-plate reader (Bio-Tek). For Michaelis-Menten curve plotting, initial velocity was calculated using linear regression of the progress curve linear segment, adjusted to RLU/min. For caspase-3 inhibition capability, caspase-3 inhibitor drug detection kit (Abcam) was performed according to the manufacturer's instructions.

Brain Lysate Preparation and Western Blotting:

The rodents were placed under 12 hour light/dark conditions and housed in individually ventilated cages with ad libitum access to food and water. For brain lysate preparation, FVB/N BACHD mice and their wild-type littermates were euthanized by de-capitation. Striata were dissected and placed in lysis buffer (200 mM HEPES, 150 mM NaCl, 1 mM $Na_3Vo_4$, 5 mM EDTA, 1% NP-40, 0.5% DOC, 50 mM NaF) with protease inhibitors (Roche) for 1 hour on ice. Tissue debris was removed by to centrifugation at 20,000×g for 15 min at 4° C. Protein concentration was determined by the BCA method (Pierce). 50 µg of lysate proteins were exposed to 100 U/ml purified active human caspase-6 for 20 minutes in 37° C. in the presence of 50 µM ED11 or DMSO as vehicle control. Lysates were subsequently loaded on 7.5% SDS-PAGE gels and transferred to 0.45 µM nitrocellulose membranes. The membranes were probed with mouse anti-Htt 2166 (1:2000, Millipore), rabbit anti-Htt 4-19 (1:1000, CHDI), and mouse anti β-actin (1:10000, Sigma). Secondary antibodies used were IRDye 800CW Goat anti-Mouse IgG, IRDye 800CW Goat anti-rabbit IgG and IRDye 680RD Goat anti-Mouse IgG, respectively. Fluorescent signal was read using Odyssey imaging system.

Cell Culture:

Human neuroblastoma cells, SH-SY5Y cells (ATCC) were grown on tissue culture plates (Greiner) in Dulbecco's Modified Eagle's Medium (DMEM), supplemented with 10% fetal calf serum (FCS), 1% L-glutamine and 1% SPN antibiotics (Biological Industries Israel). Inducible 145Q-MHtt expressing PC12 cells were obtained from CHDI (by Coriell institute). Cells were grown in suspension in 75 $cm^3$ culture flasks (Corning) in Dulbecco's Modified Eagle's Medium (DMEM), supplemented with 15% Horse-serum, 2.5% FCS, 0.1 mg/ml G418 (Gibco), 0.1 mg/ml Zeocin (Invitrogen), 1% L-glutamine and 1% SPN antibiotics (Biological Industries Israel). Both cell types were incubated at 37° C. in a humidified atmosphere with 5% $CO_2$, and passaged twice a week.

Cell Proliferation and Cell Cycle Analysis:

SH-SY5Y cells were pre-incubated with 25 µM ED11 for one hour. Then, 10 µM 5-bromo-2-deoxyuridine (BrdU) was added for 2 hours. Medium was discarded and cells were fixed with 70% ethanol. DNA denaturation was conducted with 1.5 M HCl exposure for 30 minutes. FITC conjugated anti-BrdU antibody was used to mark incorporated BrdU. DNA staining was performed by using propidium iodide (PI). 15,000 cells per sample were read using FACS-Calibur flow cytometer, and cell-cycle analysis was conducted after doublet discrimination.

Glutamate Toxicity

To induce exogenous glutamate toxicity, SH-SY5Y cell were incubated with the indicated concentrations of L-Glutamate (Sigma) for 16 hours, in the presence of 20 µM ED11 or vehicle control. For the In-cell caspase-6 activity assay, green FLICA caspase-6 assay (ImmunoChemistry Technologies) was conducted according to the manufacturer's instructions. Briefly, cells were lifted by trypsin and adjusted to $1.5 \times 10^6$ cells/ml. Cells were incubated with FAM-VEID-FMK for 1 hour in 37° C., washed with PBS and 5,000 cells per sample were analyzed by flow-cytometry. For apoptosis detection, Annexin V-FITC apoptosis detection assay (Abcam) was conducted according to the manufacturer's instructions. Briefly, $2 \times 10^5$ cells were incubated with Annexin V-FITC and PI for 5 minutes in R.T, and 15,000 cells per sample were analyzed by flow-cytometry. For viability assessment, medium was depleted and washed twice with PBS, and alamar-blue dye (AbD serotec, ⅒ in culture medium) was added to the cells, as instructed by the manufacturer. Fluorescence was monitored at 530-560 nm excitation wavelength and 590 nm emission wavelength, and viability was calculated as percentage of untreated control.

Mutant Huntington Induced Toxicity

To induce mHtt expression, Inducible 145Q-mHtt expressing PC12 cells were incubated with 25 µM ponasterone a (PA, Invitrogen) for the indicated time periods, in the presence of 25 µM ED11 or vehicle as control. Cell viability was measured by alamar-blue as previously described. LDH release was measured by the LDH Cytotoxicity Detection Kit (Clonetech), following manufacturer's instructions. Briefly, PC12 cells were grown on 6-well plate at a density of $7 \times 10^5$ cells/ml, and samples were taken at the indicated time points. Subsequently, samples were centrifuged, transferred to a 96 well plate and were incubated with the reaction mixture for 30 minutes in the dark. The plate was read at 492 nm and 690 nm as reference in Synergy HT multi-mode micro-plate reader, and calculations were done in reference to a none-induced control. For FLICA caspase-6 assay, cells were adjusted to $1.5 \times 10^6$ cells/ml and were incubated with FAM-VEID-FMK for 1 hour at 37° C. as described. Hoechst stain (ICT) was used as nucleus counterstaining. The images were recorded with a fluorescence microscope (OLYMPUS). Image analysis was made by the Image-J software (Abramoff et al., 2004).

Animal Studies

To evaluate ED11 ability to provide protection from mHtt toxicity in-vivo, HD mice model BACHD was used. ED11 treatment commenced at the age of 5 weeks by a subcutaneously implanted mini-pump, which infuses continuously for 28 days, at a dose of 4 mg/kg/day.

At the age of 9 weeks, motor coordination and strength were assessed using the accelerating Rotarod test. Mice were trained for 3 consecutive days on the accelerating rod (0 to 21 RPM in 4 minutes), 3 trials per day with a 2 hours inter-trial rest. On the fourth day Mice were tested on the accelerating rod for 3 consecutive tests, and best score was taken for analysis.

Statistical Analysis

Statistical analysis was performed using GraphPad prism version 6.0. Statistical significance for differences between two groups was evaluated by unpaired student's t-test. When three groups were addressed, statistical evaluation was made by one-way ANOVA followed by Tukey's multiple-comparison post hoc test. When addressing time-points dependent alterations, two-way ANOVA with Tukey's multiple-comparison post hoc test was used. Data are presented as mean±SEM, and the level of $P<0.05$ was accepted as statistically significant.

Results

Figure 1C:
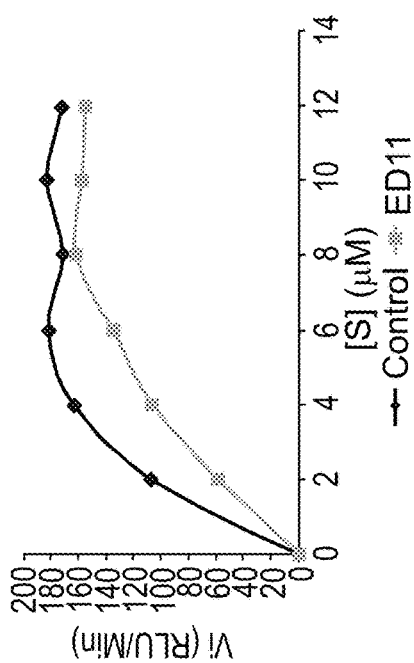
Figure 1D:
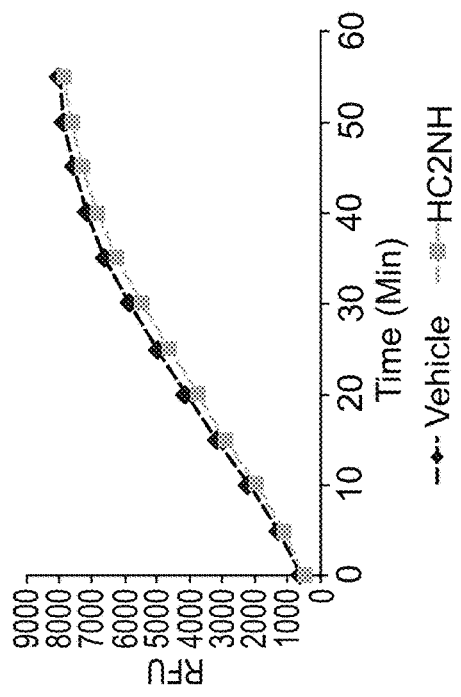
Figure 1A:
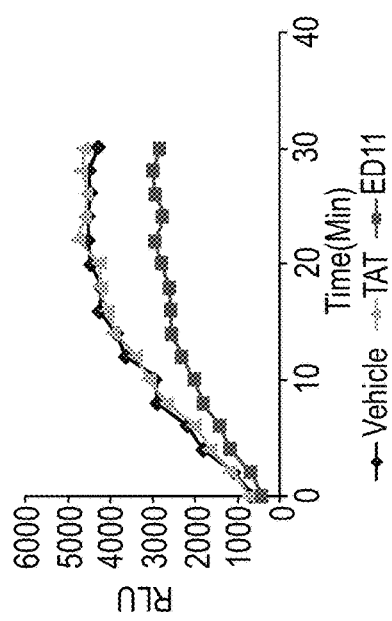
Figure 1B:
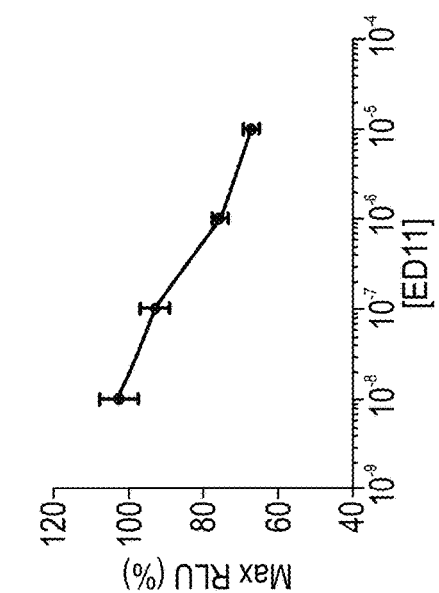

EDIT inhibits caspase-6 activity in a purified caspase-6 activity assay: To test the peptide ability to compete on caspase-6 activity, purified caspase-6 and Z-VEID-Aminoluciferin (Caspase-6 Glo™, Promega) were incubated with ED11, and bioluminescence signal was detected using SynergyHT microplate reader (FIGS. 1A-D). The peptide ED11 (GRKKRRQRRRPPQSSEIVLDGTDN—SEQ ID NO: 6) significantly reduced caspase-6 activity and using Michaelis-Menten curve it shows classic competitive inhibition as Vmax stays approximately the same and Km shows a 3.3 fold increase (FIG. 1C). In contrast, ED11 does not inhibit caspase-3 in a fluorescent caspsae-3 inhibition assay (FIG. 1D).

Figure 1E:
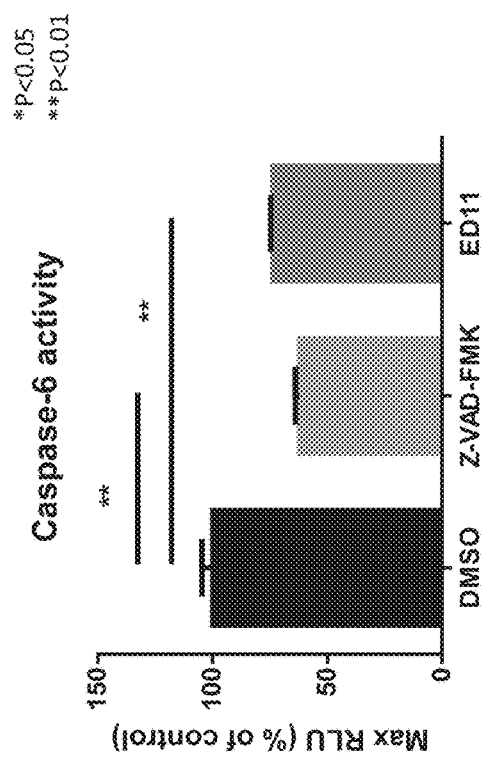
Figure 1F:
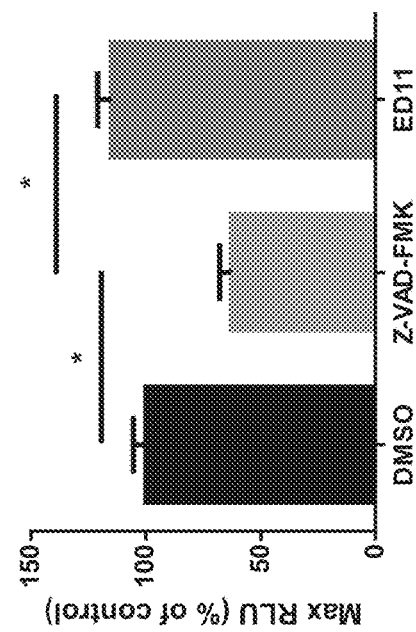

A further experiment was performed to analyze the specificity of ED11. ED11 and Z-VAD-FMK, a synthetic pan caspase inhibitor used as control, were tested in the purified caspase-3/caspase-6 assay. Here it is demonstrated that while Z-VAD-FMK inhibits activity of caspase-3 and caspase-6, ED11 inhibits activity of caspase-6 but not caspase-3 (FIGS. 1E-F).

Interestingly, when three of the amino acids in ED11 in positions 17, 20 and 23, to Histidine (H), the modified peptide was ineffective and didn't inhibit the caspase 6 activity.

ED11 does not influence cell viability, proliferation or cell cycle status in a basal state: In order to provide a preliminary safety evaluation, the influence of ED11 was tested on cell viability, proliferation and cell cycle state. ED11 was shown to have no effect on any of these parameters at a concentration up to 50 µM after 48 hours incubation (FIGS. 2A-C).

Evaluation of ED11 Caspase-6 Inhibition and Protection Against Glutamate Toxicity in a Neuroblastoma Cell Line:

The protection of ED11 (25 µM) against glutamate was tested in a neuroblastoma cell line SH-SY5Y. It was found that ED11 significantly inhibited endogenous caspase-6 activity that was induced by 17 mM glutamate, and protected the cells from apoptosis (FIGS. 3A-D).

ED11 Protects Inducible mHtt Expressing PC12 Cell-Line from mHtt Toxicity:

In order to evaluate ED11 ability to protect cells from mHtt toxicity, PC12 cells harboring an inducible mHtt expression vector (CHDI), were placed under chronic serum deprivation stress, and induced to express mHtt by 25 µM Ponasterone A (PA) for 72 hours. Cell viability was measured by Alamar blue assay, cell death by LDH assay (Clonetech), and caspase-6 activity by FLICA in-cell caspase activity. In all parameters tested, ED11 was shown to significantly avert the toxic effect of mHtt expression on the cells (FIGS. 4A-D).

ED11 Prevents Mutant Huntingtin Direct Cleavage by Caspase-6:

To test ED11's ability to interfere directly with caspase-6 cleavage of mHtt, brain striatum extracts, taken from BACHD mice were incubated with caspase-6 for 20 minutes at 37° C. The addition of ED11 significantly inhibited human mHtt fragmentation as indicated with specific anti-Htt antibodies as illustrated in FIGS. 5A-B (4-19 and MAB 2166).

Following administration of ED11, the present inventors showed that the peptide was effective at protect the BACHD mice from motor deterioration as was tested in the accelerating Rotarod test (FIGS. 7A-C).

Relevance of amino acids X1 and X4:

In order to test whether the amino acids at position X1 and X4 are important for peptide activity, three additional peptides were to synthesized which had substitutions at positions X1 and X4 and their ability to inhibit caspase 6 was analyzed.

As illustrated in FIG. 8, substitutions at either position X1 and X4 were detrimental to the ability of the peptide to inhibit caspase 6.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of treating Huntington's Disease (HD) in a subject in need thereof, the method comprising administering to the subject a therapeutically effective amount of an isolated peptide comprising a Huntingtin (Htt) amino acid sequence being no longer than 15 amino acids which comprises the sequence as set forth in SEQ ID NO: 2, thereby treating the Huntington's Disease (HD).

2. The method of claim 1, wherein said Htt amino acid sequence is attached to a cell penetrating agent.

3. The method of claim 2, wherein said cell penetrating agent is a cell penetrating peptide agent.

4. The method of claim 3, wherein said cell penetrating peptide agent is attached to said Htt amino acid sequence via a linking amino acid sequence.

5. The method of claim 4, wherein said linking amino acid sequence comprises a disulfide bridge.

6. The method of claim 4, wherein said linking amino acid sequence is attached to the N terminal of said Htt amino acid sequence.

7. The method of claim 5, wherein said linking amino acid sequence comprises the sequence SSE.

8. The method of claim 1, wherein said Htt amino acid sequence inhibits the activity of caspase 6 to a greater extent than it inhibits the activity of caspase 3.

9. A method of treating Huntington's Disease (HD) in a subject in need thereof, the method comprising administering to the subject a therapeutically effective amount of the isolated peptide as set forth in SEQ ID NO: 6, thereby treating the Huntington's Disease (HD).

10. The method of claim 1, wherein said Htt amino acid sequence is no longer than 11 amino acids.

* * * * *